United States Patent
Lamparski et al.

(10) Patent No.: US 6,812,023 B1
(45) Date of Patent: Nov. 2, 2004

(54) METHODS OF PRODUCING MEMBRANE VESICLES

(75) Inventors: Henry Lamparski, San Mateo, CA (US); Curtis Ruegg, Redwood City, CA (US); Jean-Bernard Le Pecq, Menlo Park, CA (US); Di-Hewi Hsu, Sunnyvale, CA (US); Jenq Yuan Yao, Mountain View, CA (US)

(73) Assignee: Anosys, Inc., Menlo Park, CA (US)

( * ) Notice: Subject to any disclaimer, the term of this patent is extended or adjusted under 35 U.S.C. 154(b) by 0 days.

(21) Appl. No.: 09/561,205

(22) Filed: Apr. 27, 2000

(51) Int. Cl.$^7$ .................................................. C12N 5/06
(52) U.S. Cl. .................. 435/325; 435/355; 435/371; 435/372; 435/372.1; 435/820
(58) Field of Search ................. 435/325, 355, 435/371, 372, 372.1, 820

(56) References Cited

PUBLICATIONS

Chao et al, Blood, 55,187, 1980.*
Zala et al, Biochim Biophys Acta, 600, 157, 1980.*
5562, Dendritic Cell (DC)–Derived Exosomes (DEX) Activate T Cells Similar to DC: Implications for Novel Tumor Vaccines, Di–Hwei Hsu et al., AP Cells, Menlo Park, CA.
5556 Dendritic Cell–Derived Exosomes (DEX) Are Effective Cancer Vaccines: Preclinical Data Towards A Clinical Trial, J. Wolfers et al. AP Cells, Inc., Menlo Park, CA and Inst. Curie, Paris France.

* cited by examiner

Primary Examiner—David Saunders
(74) Attorney, Agent, or Firm—Orrick, Herrington & Sutcliffe LLP

(57) ABSTRACT

The present invention relates to methods of preparing biological material, for use in various experimental, diagnostic or therapeutic uses, including immunotherapy treatment or prophylaxy of tumors. More particularly, the present invention relates to methods of preparing membrane vesicles (in particular exosomes) released by various types of mammalian cells, comprising diafiltration and/or density cushion centrifugation. The invention also provides novel methods for characterizing and analyzing exosome preparations, which can be used in quality control assay for the purpose of pharmaceutical product production. The invention is suitable to produce pharmaceutical grade preparations of such membrane vesicles and to fully characterize said preparations, for use in human beings.

9 Claims, 29 Drawing Sheets

Figure 1:
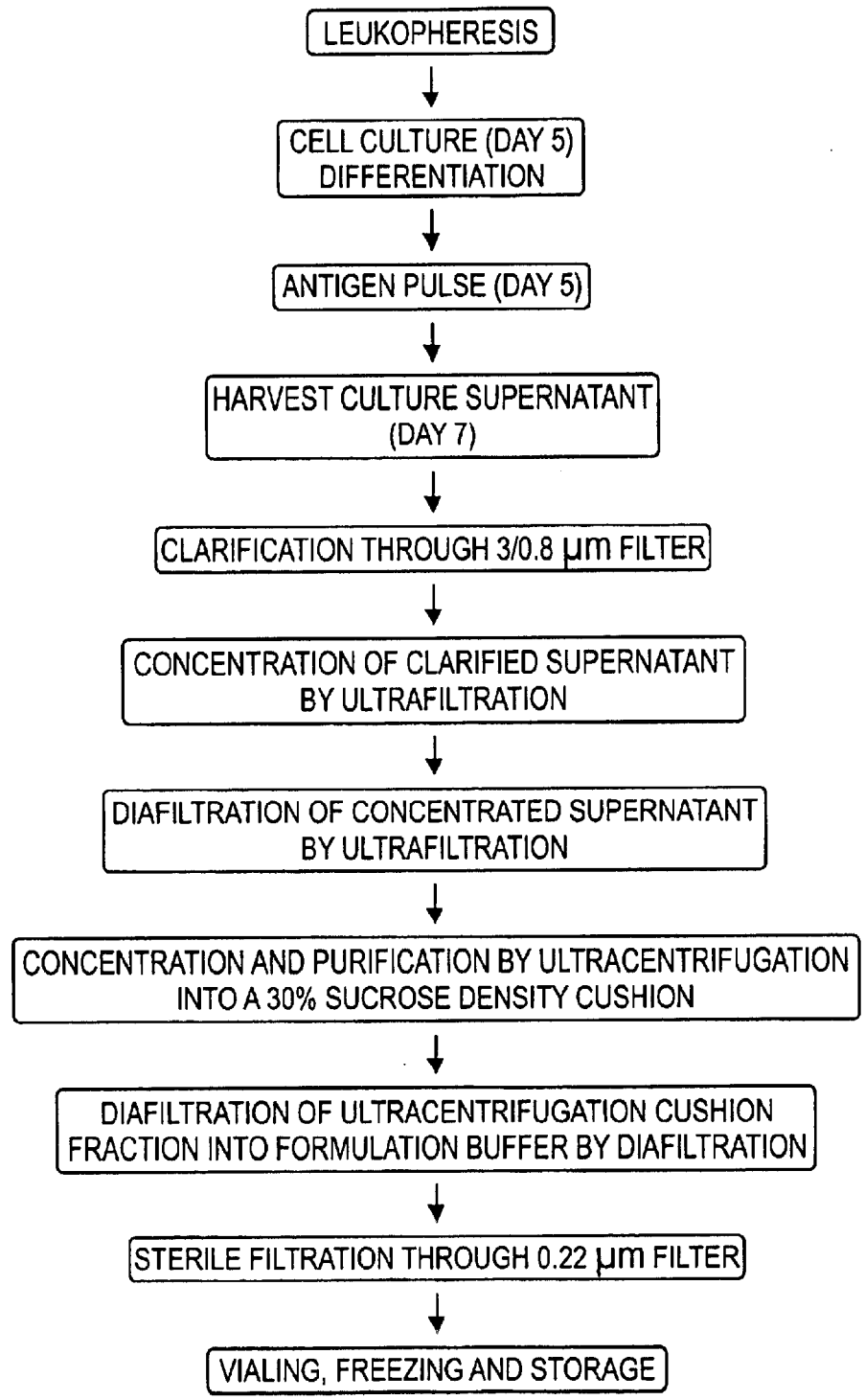

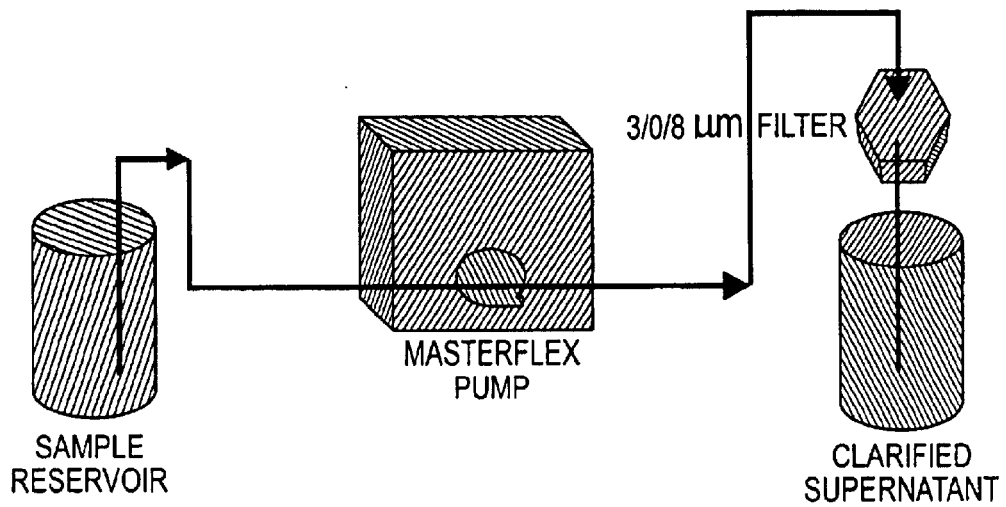
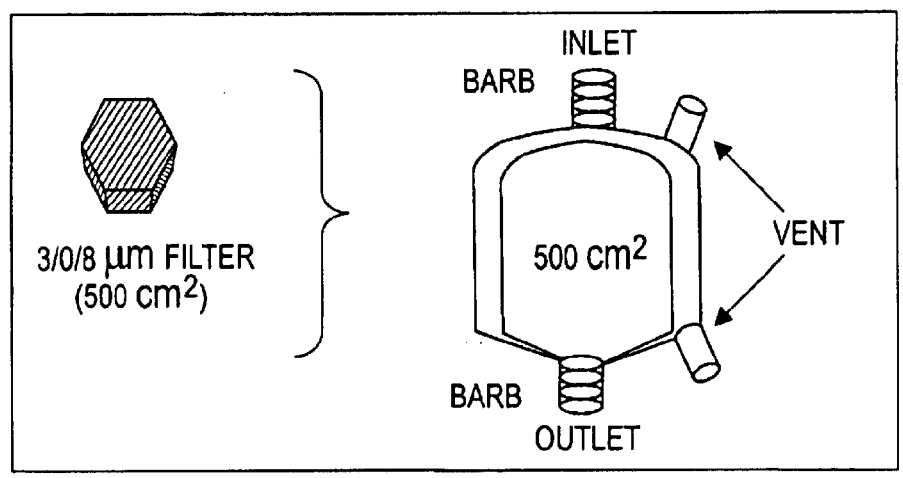
FIG. 5

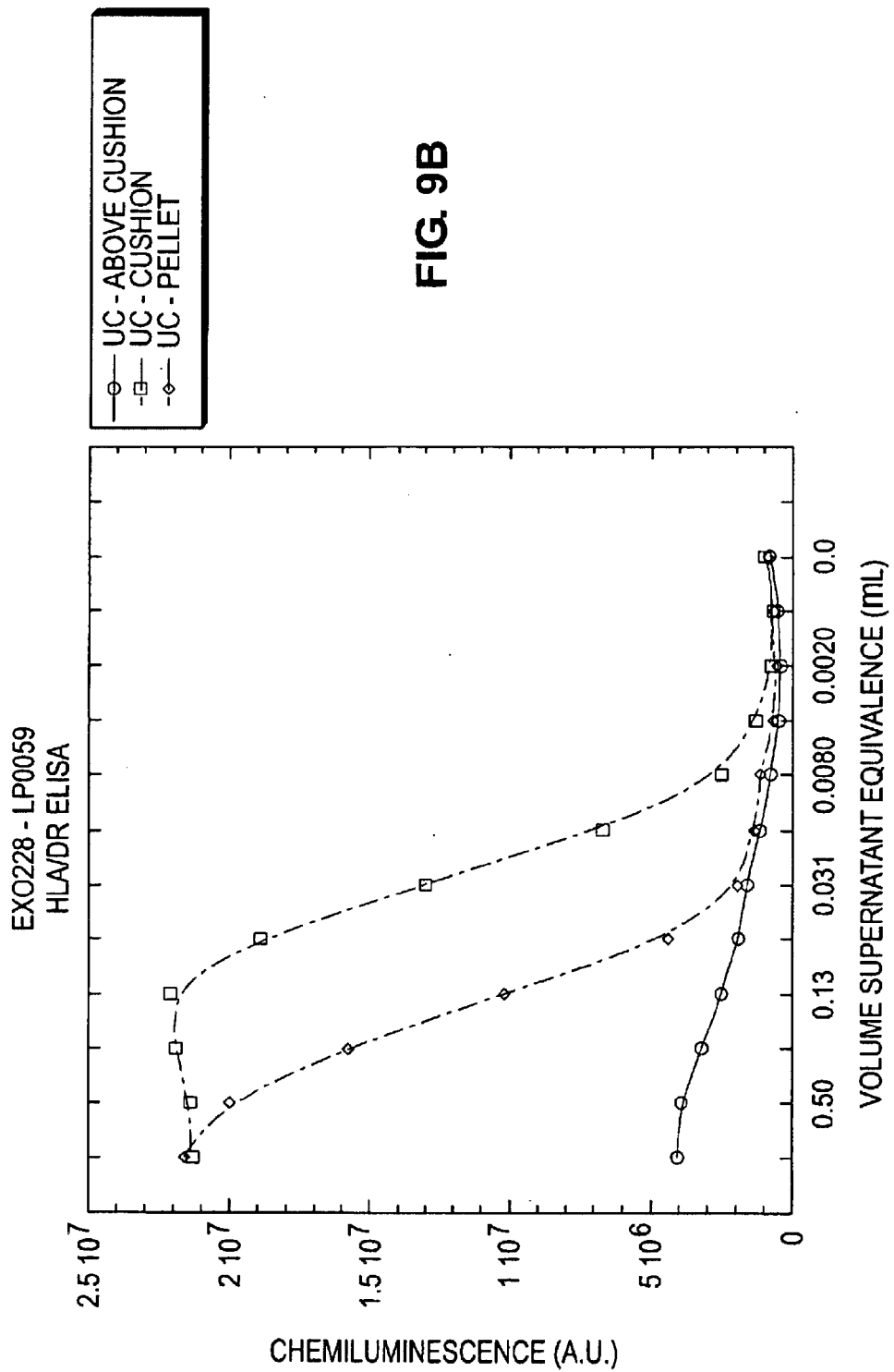

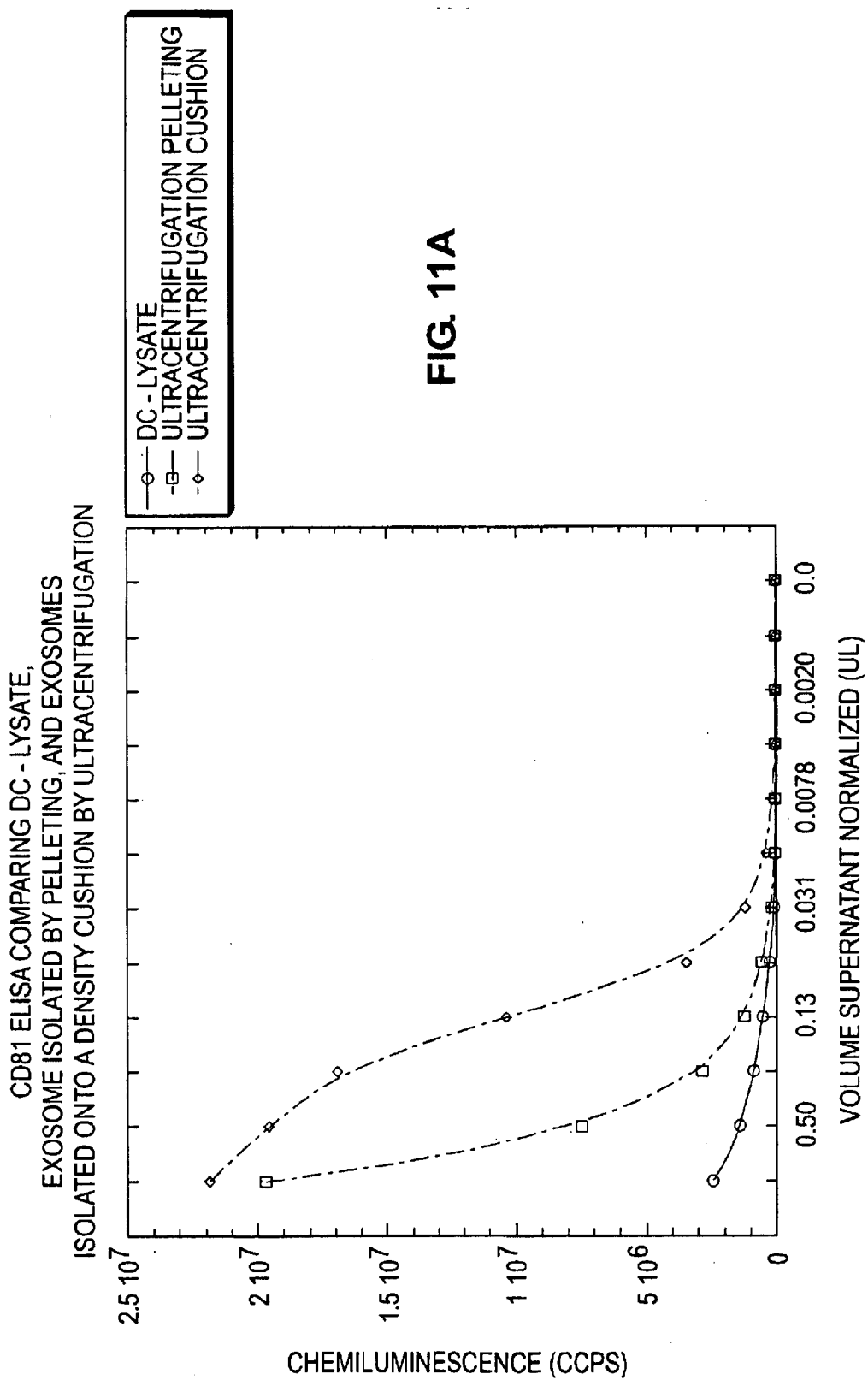

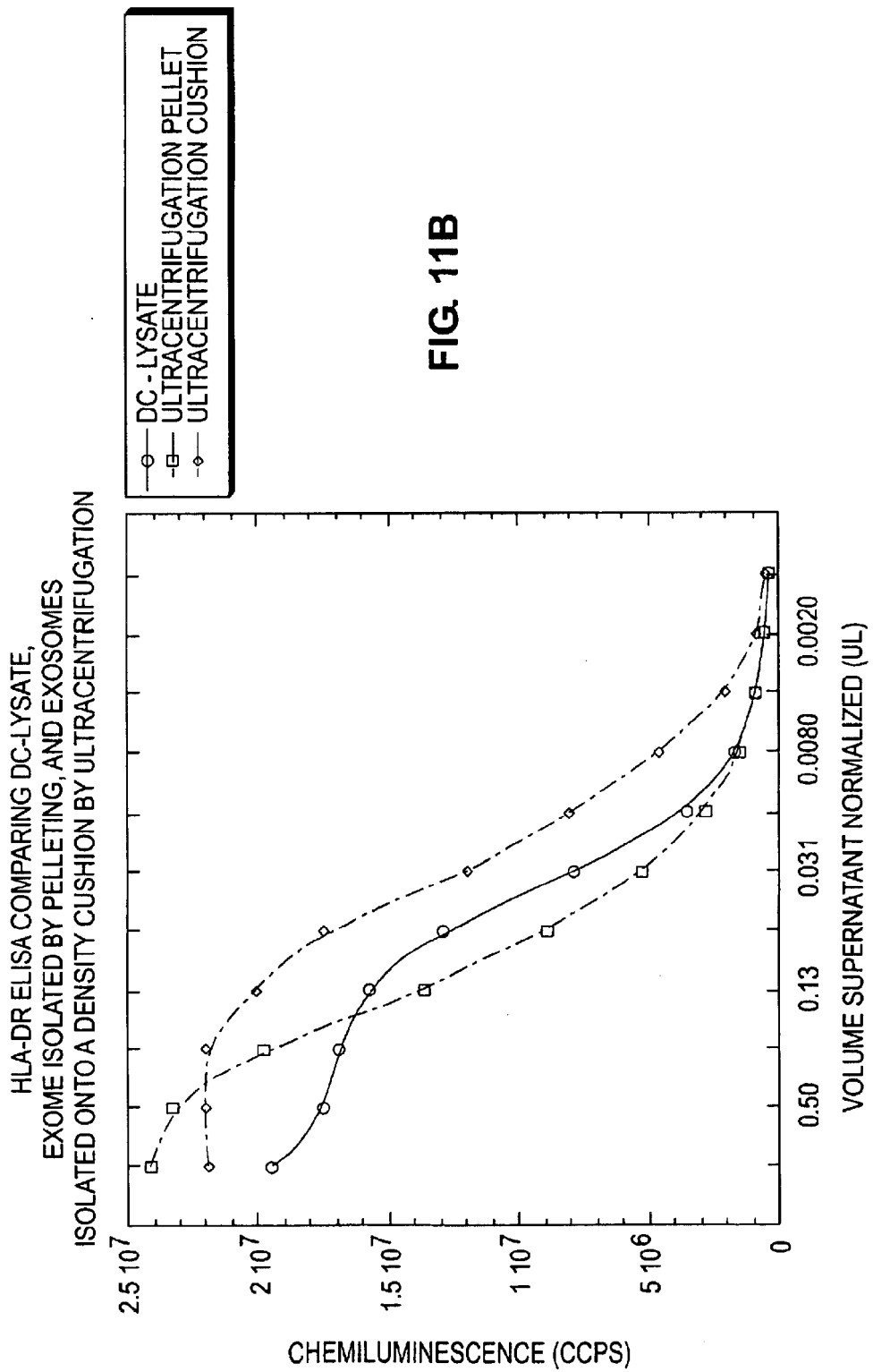

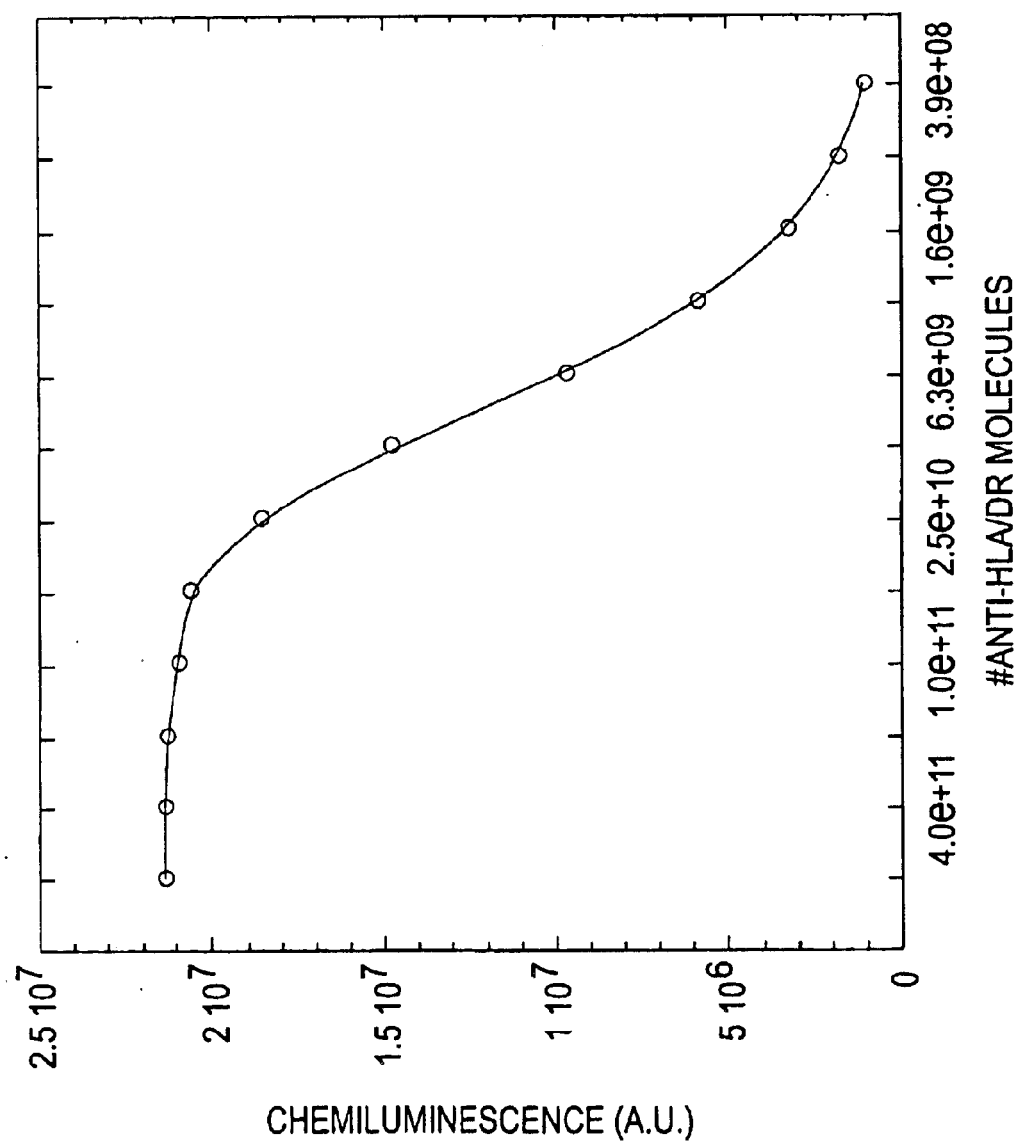

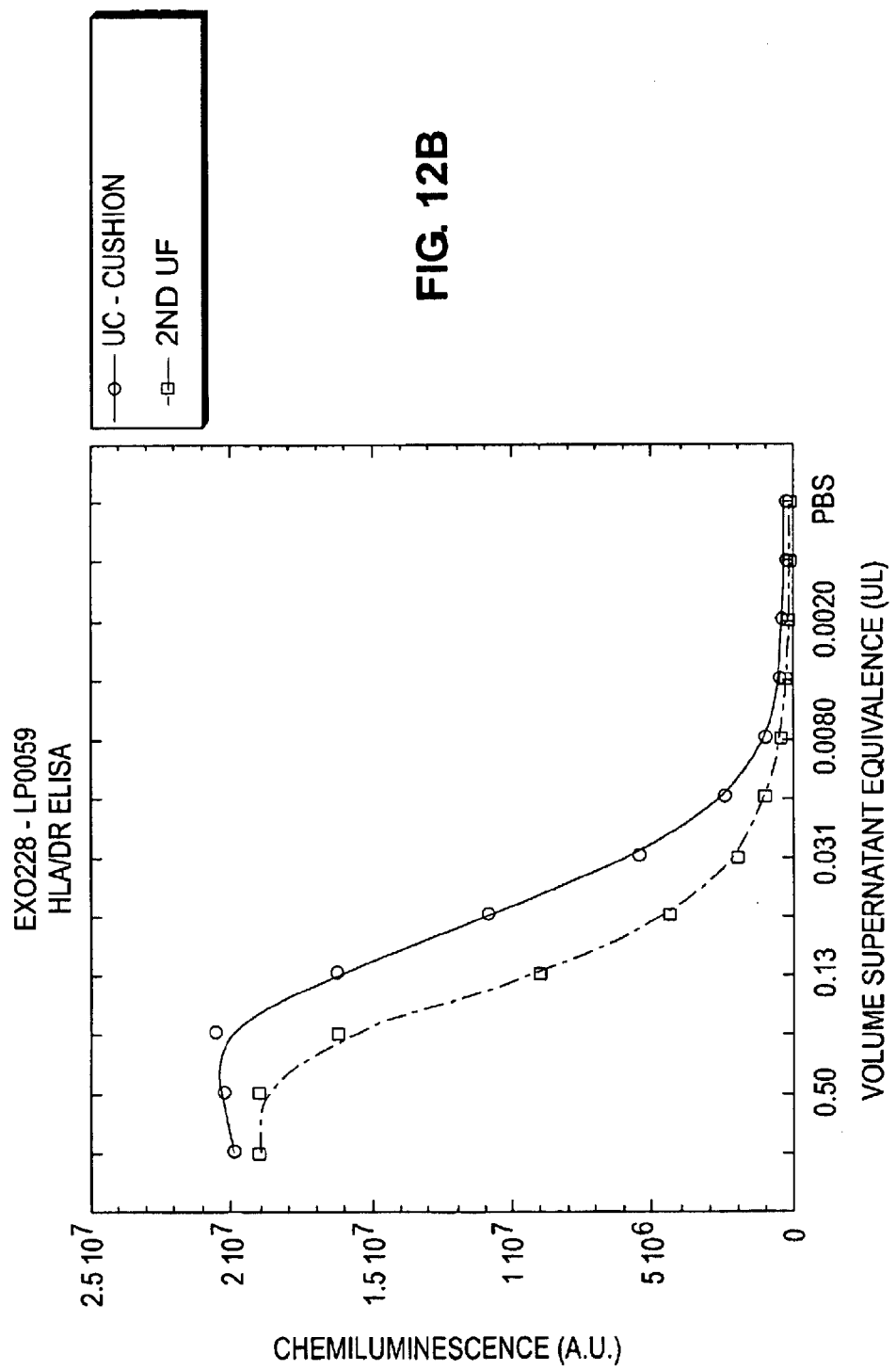

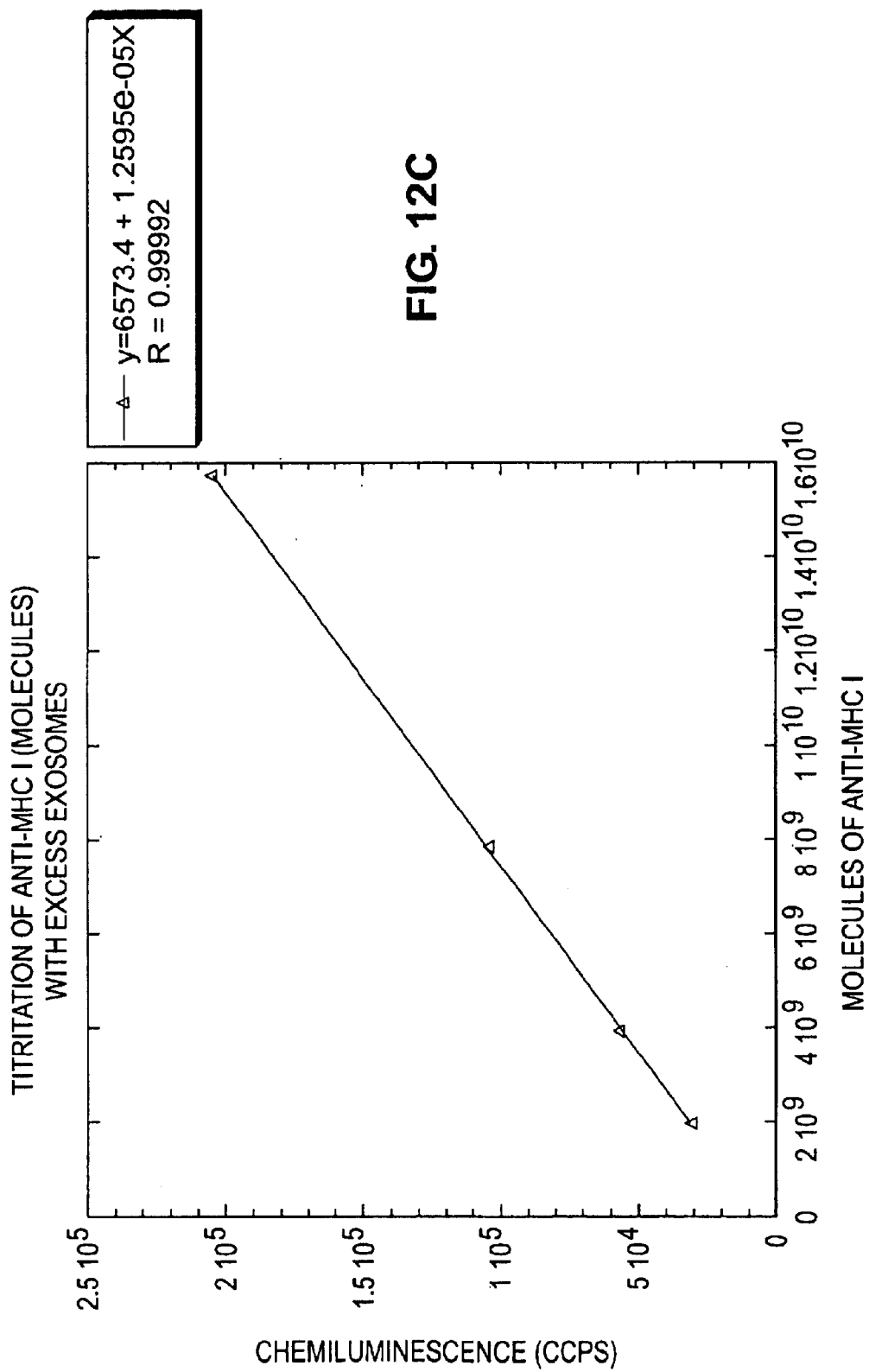

METHODS OF PRODUCING MEMBRANE VESICLES

FIELD OF INVENTION

The present invention relates to methods of preparing biological material, for use in various experimental, diagnostic or therapeutic uses, including immunotherapy treatment or prophylaxy of tumors. More particularly, the present invention relates to methods of preparing membrane vesicles (in particular exosomes) released by various types of mammalian cells, comprising diafiltration and/or density cushion centrifugation. The invention also provides novel methods for characterizing and analysing exosome preparations, which can be used in quality control assay for the purpose of pharmaceutical product production. The invention is suitable to produce pharmaceutical grade preparations of such membrane vesicles and to fully characterize said preparations, for use in human beings.

BACKGROUND OF THE INVENTION

Membrane vesicles are essentially spherical vesicles, generally less than 130 nm in diameter, composed of a lipid bilayer containing a cytosolic fraction. Particular membrane vesicles are more specifically produced by cells, from intracellular compartments through fusion with the plasmic membrane of a cell, resulting in their release in biological fluids or in the supernatant of cells in culture. Such vesicles are generally referred to as exosomes. Exosomes are more particularly between about 30 and about 120 nm, preferably 50 and 90 nm, more specifically between about 60 and 80 nm in diameter and, advantageously, carry membrane proteins (particularly major histocompatibility complex proteins or other protein which directly or indirectly participate in antigen presentation). In addition, depending on their origin, exosomes comprise membrane proteins such as MHC I, MHC II, CD63, CD81 and/or HSP70 and have no endoplasmic reticulum or Golgi apparatus. Furthermore, exosomes are void of nucleic acids (e.g. DNA or RNA).

Exosome release has been demonstrated from different cell types in varied physiological contexts. In particular, it has been demonstrated that B lymphocytes release exosomes carrying class II major histocompatibility complex molecules, which play a role in antigenic presentation (Raposo et al., J. Exp. Med. 183 (1996) 1161). Similarly, it has been demonstrated that dendritic cells produce exosomes (i.e., dexosomes, Dex), with specific structural and functional characteristics and playing a role in immune response mediation, particularly in cytotoxic T lymphocyte stimulation (Zitvogel et al., Nature Medicine 4 (1998) 594). It has also been demonstrated that tumor cells secrete specific exosomes (i.e., texosomes, Tex) in a regulated manner, carrying tumor antigens and capable of presenting these antigens or transmitting them to antigen presenting cells (patent application No. WO99/03499). It is also known that mastocyte cells accumulate molecules in intracellular vesicular compartments, which may be secreted under the effect of signals (Smith and Weis, Immunology Today 17 (1996) 60). Therefore, as a general rule, cells appear to emit signals and communicate with each other via membrane vesicles that they release, which may carry antigenic proteins (or polypeptides or peptides), MHC molecules or any other signal (cytokine, growth factor, etc.) with specific structural and functional characteristics, produced in different physiological situations. These vesicles, particularly exosomes, thus represent a product of particular interest for diagnostic, vaccination or therapeutic applications or to deliver molecules of interest. Therefore, it would be of particular interest to have an effective method that could be used at an industrial scale to prepare membrane vesicles compatible with biological use, particularly pharmacological use.

Conventional methods to prepare membrane vesicles (e.g. exosomes) involve a series of differential centrifugation steps to separate the vesicles from cells or cell debris present in the culture medium. In this regard, the documents mentioned above essentially describe the preparation of vesicles with a series of centrifugations at 300 g, 10,000 g and 70,000 g or 100,000 g, upon which the resulting pellet at the bottom of the tube is resuspended to $\frac{1}{1000}^{th}$ its original volume with a saline solution to constitute a concentrated exosome solution. However, these methods are essentially unsuitable for clinical applications for a number of reasons: 1) length of time, 2) scale-up and validation in GMP environment, 3) significant risk of contamination by cell debris, 4) poor reproducibility due to operator variability, 5) aggregation of exosomes resulting from pelleting (high localized exosome concentration in pellet) and 6) low recovery at end of processing. There is therefore a need for improved methods of preparing membrane vesicles, suitable with industrial constraints and allowing production of vesicle preparations of therapeutic quality.

International application n° PCT/FR00/00105 discloses methods of preparing membrane vesicles through chromatographic techniques, such as anion exchange chromatography and/or gel permeation chromatography.

SUMMARY

The present invention now provides novels methods of preparing membrane vesicles in high yields, high purity, and in relatively short periods of time. The present invention also discloses methods of characterizing (or analyzing or dosing) a membrane vesicle preparation, which can be used in pharmaceutical production to determine the activity, phenotype and/or quantity of vesicles. The invention now allows the production and characterization of clinically acceptable lots of membrane vesicles, with reproducibility, limited operator variation, and increased product quality. This invention further relates to methods of removing particulate bodies, such as haptoglobin, from various medium or compositions, the resulting compositions and media and their uses.

More specifically, an aspect of the present invention resides in methods of preparing membrane vesicles using density cushion centrifugation.

Another aspect of the present invention resides in methods of preparing membrane vesicles using a series of ultrafiltration steps and/or clarification step, more specifically a combination of a concentration and diafiltration by ultrafiltration, preferably preceded by a clarification.

Another aspect of this invention resides in methods of preparing membrane vesicles using a combination of density cushion centrifugation and ultrafiltration and/or clarification step, more specifically a combination of a concentration and diafiltration by ultrafiltration, preferably preceded by a clarification, followed by density cushion centrifugation.

In a particular aspect, the method of this invention comprises a density cushion centrifugation preceded or followed by a diafiltration.

The method of this invention can be applied to various biological samples containing membrane vesicles, including a biological fluid, a culture supernatant, a cell lysate or a pre-purified solution. In a particular embodiment, the method is used to prepare (e.g., purify or separate or isolate) membrane vesicles from a biological sample enriched with membrane vesicles.

A particular aspect of the present invention resides in a method of preparing membrane vesicles from a biological sample, comprising:
   a. the culture of a population of membrane vesicle-producing cells under conditions allowing the release of the vesicles,
   b. a membrane vesicle enrichment step, and
   c. the treatment of said enriched biological sample by density cushion centrifugation.

In a further preferred embodiment, the membrane vesicle-producing cells are cultured in a culture medium with reduced particulate bodies' content, preferably a medium deprived of haptoglobin aggregates. As will be demonstrated in this application, the use of such a medium allows increased production yields and/or higher purity and quality levels to be achieved.

The enrichment step may comprise one or several centrifugation, clarification, ultrafiltration, nanofiltration, affinity chromatography and/or diafiltration steps. More preferably, the enrichment step comprises a clarification and/or a concentration and/or a diafiltration.

The preparation of exosomes may be collected from step c) by any appropriate means, including pipetting or with a needle.

In a preferred embodiment, the method further comprises a sterile filtration d) of the preparation from step c.

The present invention can be used to prepare membrane vesicles from various origins, including membrane vesicles produced by antigen-presenting cells (such as macrophages, dendritic cells, B lymphocytes), tumor cells or any other cell or cell line producing vesicles, preferably transduced for antigens. It is particularly suited for preparing membrane vesicles produced by dendritic cells, preferably immature dendritic cells (i.e., dexosomes). Furthermore, the membrane vesicles or corresponding producing cells can be sensitized to one or several antigens, prior to, during or after preparation.

More preferred embodiments of this invention comprise:
   a method of preparing membrane vesicles, comprising:
      b. the culture of a population of antigen-presenting cells, in particular dendritic cells, under conditions allowing the release of membrane vesicles by antigen-presenting cells, in particular dendritic cells,
      c. a membrane vesicle enrichment step, and
      d. the isolation of the membrane vesicles using density cushion centrifugation.
   a method of preparing membrane vesicles, comprising:
      a. obtaining a population of immature dendritic cells
      b. culturing the population of immature dendritic cells under conditions allowing the release of membrane vesicles by immature dendritic cells,
      c. a membrane vesicle enrichment step, and
      d. the isolation of the membrane vesicles using density cushion centrifugation.

As indicated above, an additional step of sensitization of the vesicles (or producing cells) to one or several particular antigens can be introduced in the process, either before step b), to sensitize the producing cells, or after step b), to sensitize directly the membrane vesicles.
   a method of preparing membrane vesicles, comprising:
      a. obtaining a population of antigen-presenting cells, more preferably immature dendritic cells,
      b. sensitizing the antigen-presenting cells, more preferably the immature dendritic cells to one or several antigens,
      c. culturing the population of antigen-presenting cells, more preferably immature dendritic cells under conditions allowing the release of membrane vesicles by antigen-presenting cells, more preferably immature dendritic cells,
      d. a clarification of the culture supernatant,
      e. a concentration of the clarified supernatant,
      f. a diafiltration of the concentrated supernatant,
      g. the isolation of the membrane vesicles using density cushion centrifugation, and
      h. a sterile filtration of the membrane vesicles obtained in g.

Sterile filtration h) may be preceded by a buffer exchange step, for instance through diafiltration. A typical process scheme is depicted on FIG. 1.

Furthermore, the present invention also provides methods of removing particulate bodies from various media or compositions. More particularly, the invention demonstrates that conventional culture media contain particulate bodies, such as haptoglobin and related polymers (e.g., haptoglobin aggregates), and discloses methods of removing the same. More generally, the methods allow the production of culture media or any other biological products, such as blood proteins or polypeptides (or derivatives thereof), formulation solutions, fetal calf serum, etc., that are essentially deprived of haptoglobin aggregates.

Haptoglobin aggregates can exhibit immunosuppressive activity and thus affect the biological properties, safety and purity of membrane vesicles or other biological products, as will be further documented below. However, the issue of particular bodies was not addressed in the art, their presence in various biological products not determined, and efficient methods of removing the same not available. The invention now provides efficient methods to prepare high quality biological products, said resulting products also representing objects of this invention.

In this regard, the invention resides, generally, in a composition comprising a mammalian cell culture medium essentially free of particulate bodies, more preferably of haptoglobin aggregates.

The invention also resides in a cell culture medium deprived of haptoglobin aggregates.

The invention further resides in a composition of matter comprising antigen presenting cells (or any other membrane-vesicle producing cell, in particular dendritic cells) in a culture medium having a reduced particulate bodies content, more specifically that is essentially free of haptoglobin aggregates. More preferably, the culture medium is a culture medium treated to remove particulate or aggregate compounds, more particularly through ultrafiltration.

Another aspect of the present invention resides in method of producing or culturing antigen-presenting cells (or any membrane vesicle-producing cell), in particular dendritic cells, using culture or production media with reduced particulate bodies content. More preferably, the culture medium is a culture medium that is essentially free of haptoglobin aggregates, more specifically treated by ultrafiltration.

The invention is also suitable for the production of compositions of blood products that are essentially free of aggregated haptoglobin, as well as to the treatment of various buffer solutions prior to formulating products for pharmaceutical uses.

In this respect, the present invention also relates to a composition comprising a blood polypeptide or a derivative thereof, that is essentially deprived of haptoglobin aggregates. More particularly, this invention resides in a composition comprising a heat inactivated blood product that is essentially deprived of haptoglobin aggregates. Even more preferably, this invention relates to a composition of (heat inactivated) serum-albumin, more preferably human serum-albumin, essentially free of aggregated haptoglobin.

The invention also resides in a method of treating a biological product, more preferably a heat inactivated biological product, in order to reduce the amount of haptoglobin aggregates contained therein, comprising subjecting the product to filtration, more preferably ultrafiltration.

A particular object of this invention also resides in a method of preparing a biological product comprising (i) a heat inactivation of the biological product and (ii) a filtration of the heat inactivated biological product. More preferably, the method further comprises the step of (iii) concentrating the filtered, heat inactivated biological product and/or (iv) the conditioning thereof. The method can be used for various biological products including any protein or polypeptide (or derivatives thereof) isolated (or extracted) from mammalian biological fluids such as human blood or plasma or serum. As will be further documented in this application, this method allows, for the first time, the production of heat inactivated biological products having a reduced content in haptoglobin aggregates, more preferably essentially free of haptoglobin aggregates and thus with increased safety. The method is particularly suited for the preparation of pharmaceutical proteins extracted from blood or plasma such as serum-albumin, more preferably a human serum-albumin, gamma immunoglobulin, coagulation factors, etc.

The invention also resides in a method of treating a serum preparation, more preferably a fetal calf serum preparation, to reduce the amount of haptoglobin aggregates contained therein, comprising subjecting the preparation to filtration, more preferably ultrafiltration.

As will be further documented below, the expression "essentially free" indicates that the composition or medium contains less than about 1 ppm of haptoglobin aggregates, more preferably less than about 0.5 ppm, even more preferably no detectable haptoglobin aggregates by SDS PAGE analysis as well as by quantitative ELISA.

Another aspect of this invention resides in methods of analyzing or characterizing (or dosing) membrane vesicles in a preparation, in order to determine their phenotype and/or activity and/or quantity.

More particularly, an aspect of this invention lies in a method of characterizing membrane vesicles, comprising contacting the membrane vesicles in parallel with two or more antibodies specific for marker components of membrane vesicles and determining the formation of antigen-antibody immune complexes.

Another particular aspect comprises a method of characterizing the activity of a preparation of membrane vesicles, comprising contacting super-antigen-loaded vesicles with T cells in the presence of accessory cells, and determining the activation of the T cells.

The invention also provides a method of dosing membrane vesicles in a sample, comprising (i) loading the sample onto a solid support, (ii) contacting the support with an anti-class II antibody (or other relevant antibodies) and, (iii) determining the presence of antibody-antigen immune complexes.

The invention also comprises compositions comprising (i) membrane vesicles, (ii) a buffering agent aid (iii) a cryoprotectant or a stabilizing compound.

Other aspects of the present invention include kits, diagnostic assays, compositions of membrane vesicles, device(s) for preparing membrane vesicles, or antigen-loaded antigen-presenting cells (such as dendritic cells) or membrane vesicles.

The invention is particularly suited for preparing dexosomes (i.e., membrane vesicles produced by dendritic cells) or texosomes (i.e., membrane vesicles produced by tumor cells), more particularly of human origin. These membrane vesicles can be used in various experimental, biological, therapeutic, diagnostic or prophylactic applications. In particular, the membrane vesicles can be used to modulate an immune response in a subject, in particular in pathological conditions such as cancers, auto-immune diseases, allergy, asthma, inflammation and the like.

LEGEND TO THE FIGURES

FIG. 1. Overview of Particular Process for Autologous Dexosome Isolation and Purification.

Figure 2:
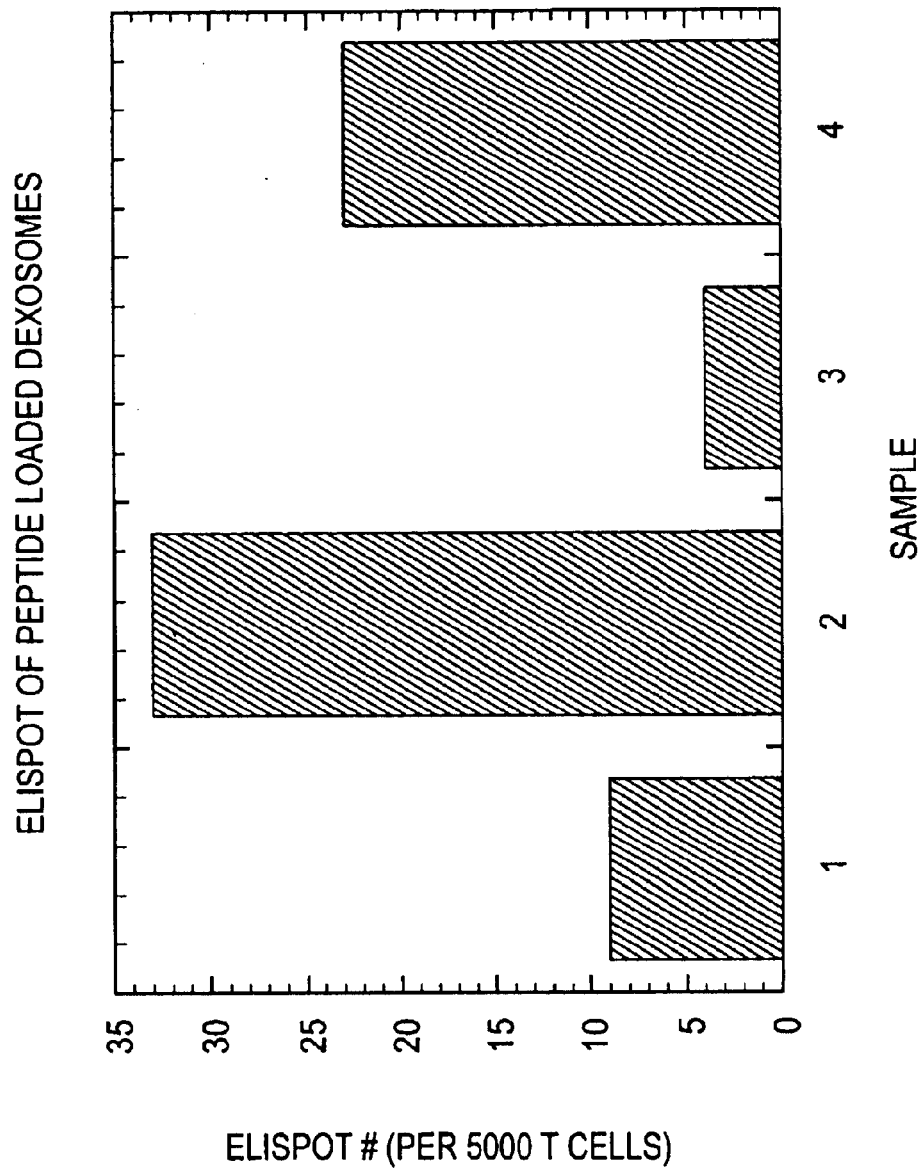

FIG. 2. DC were cultured in the presence of CMV pp65 HLA-A2 restricted peptide on Day 5. Dexosomes were harvested on Day 7 and purified. Purified CMV peptide-pulsed dexosomes were then added to a CMV pp65 HLA-A2 restricted T cell line in the presence of HLA-A2 positive or HLA-A2 negative DC. Cell cultures were conducted in ELISPOT format where culture wells were coated with antibody specific for IFN-γ and the presence of cells specifically secreting this cytokine were enumerated as a measure of T cell activation. Samples are as follows:
1. T+A2$^+$DC+exo/A2$^+$DC/No peptide
2. T+A2$^+$DC+exo/A2$^+$DC/CMV peptide
3. T+A2$^-$DC+exo/A2$^+$DC/No peptide
4. T+A2$^-$DC+exo/A2$^+$DC/CMV peptide The specific peptide response of T cells to Dexosomes can be viewed by comparing sample 2 to sample 1 and proof that the stimulation is due to peptide incorporated in Dexosomes and not due to free peptide stimulating DC directly is illustrated by comparing sample 4 to sample 3.

Figure 3:
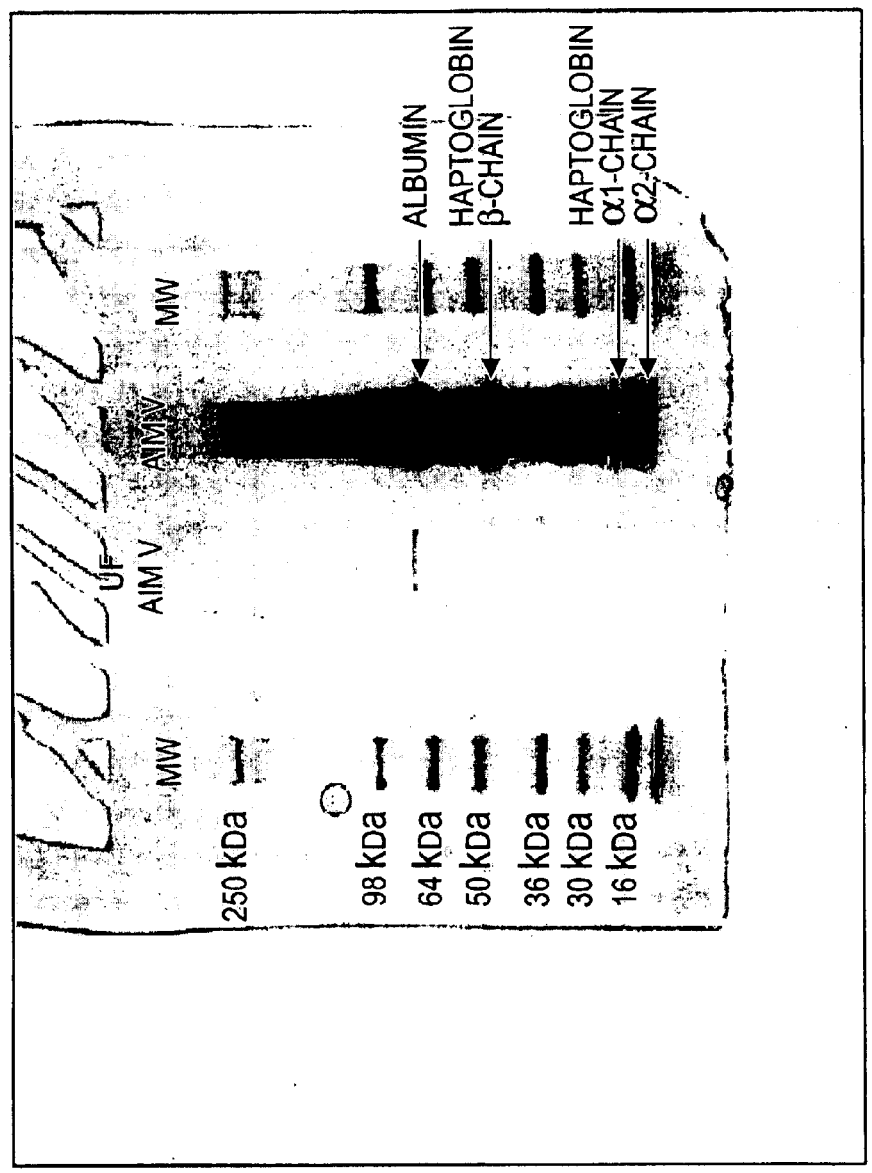

FIG. 3. SDS-PAGE of AIM V media before and after processing by ultrafiltration through 500 kDa (MWCO) hollow fiber membrane. AIM V and UF-processed AIM V were pelleted by ultracentrifugation at 100,000×g for 1 hour. The supernatant was discarded and the pellet region was resuspended in PBS and re-ultracentrifuged a $2^{nd}$ time at 100,000×g for 1 hour. The pellet was resuspended to $\frac{1}{1000}^{th}$ the original volume with PBS. 20 uL of the pellet (reducing conditions) was run on an 8–16% acrylamide gel that was subsequently stained with colloidal Coomassie Blue.

Figure 4:
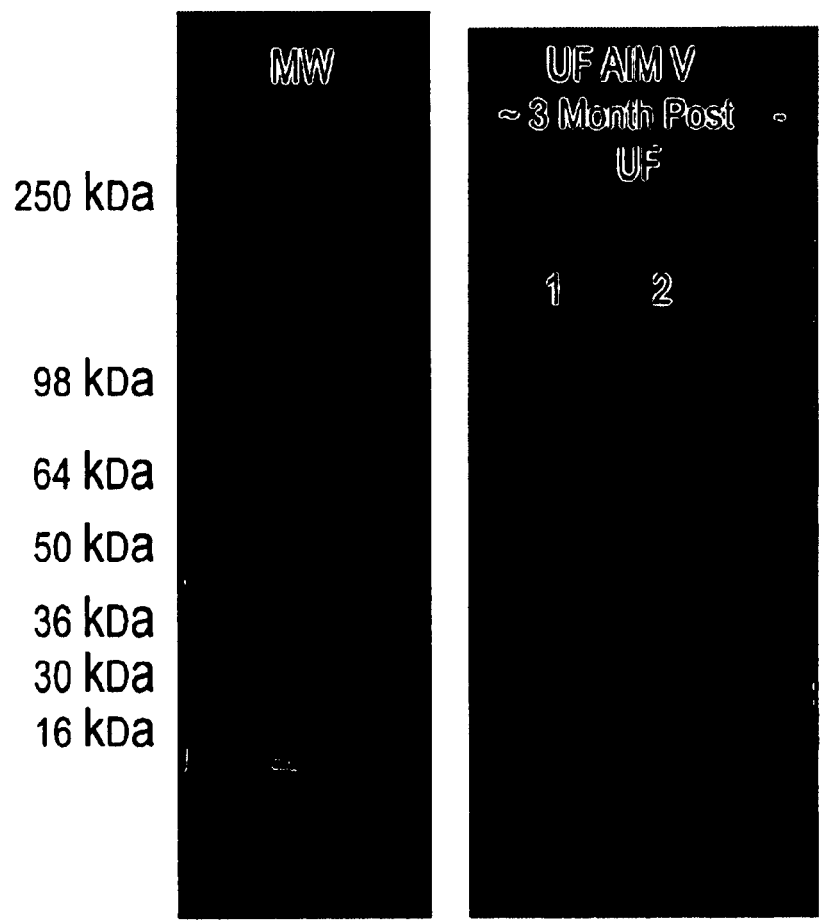

FIG. 4. SDS-PAGE of AIM V media 3 months post-processing by ultrafiltration through 500 kDa (MWCO) hollow fiber membrane. UF-processed AIM V was pelleted by ultracentrifugation at 100,000×g for 1 hour. The supernatant was discarded and the pellet region was resuspended in PBS and re-ultracentrifuged a $2^{nd}$ time at 100,000×g for 1 hour. The pellet was resuspended at $\frac{1}{1000}^{th}$ the original volume with PBS. 20 uL of the pellet (reducing conditions) was run on an 8–16% acrylamide gel that was subsequently stained with colloidal Coomassie Blue.

FIG. 5. Schematic of the microfiltration system with 3/0.8 μm capsule filter

Figure 6:
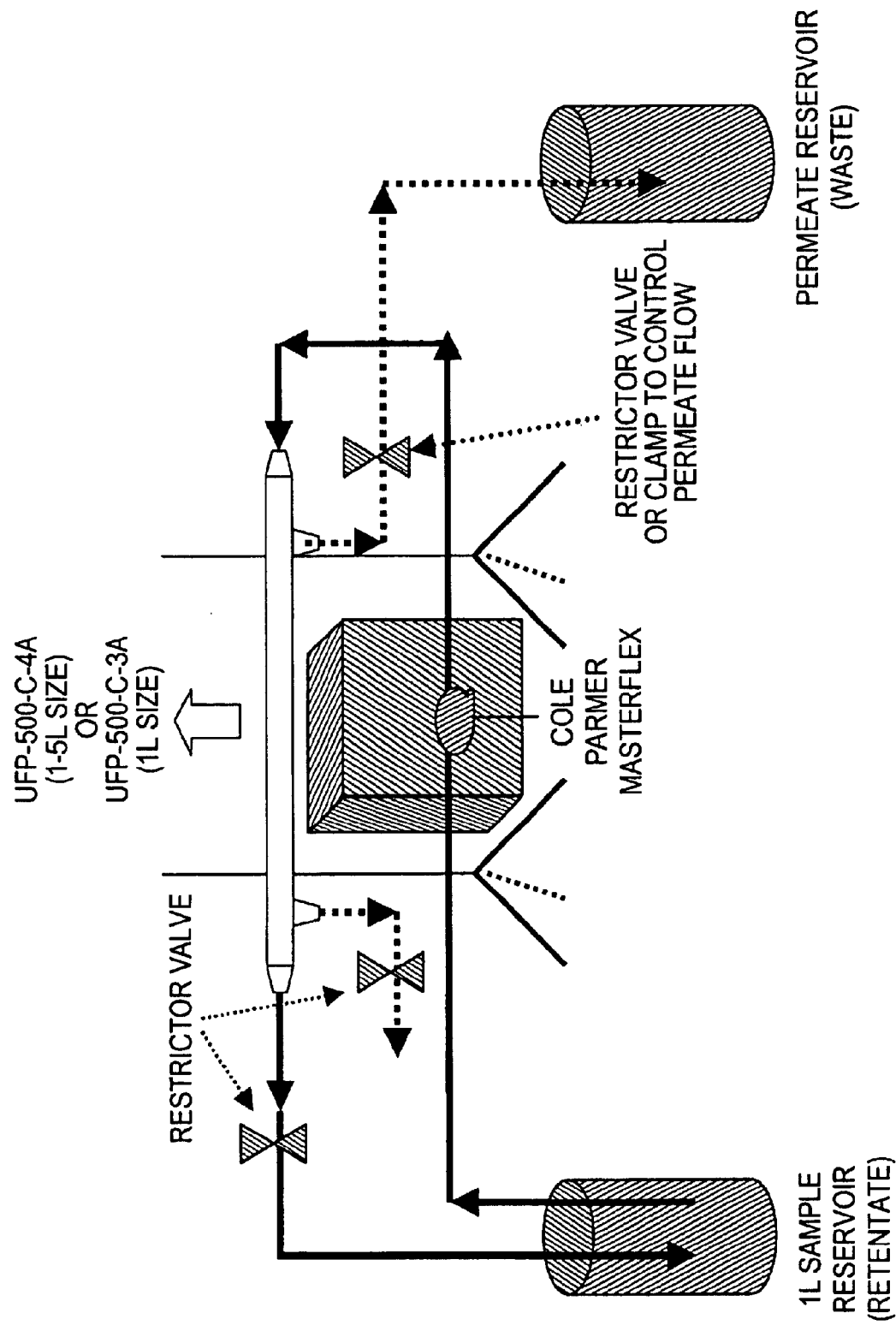

FIG. 6. Scheme: Ultrafiltration of Clarified Tissue Culture Supernatant Using a Hollow Fiber Cartridge System.

Figure 7:
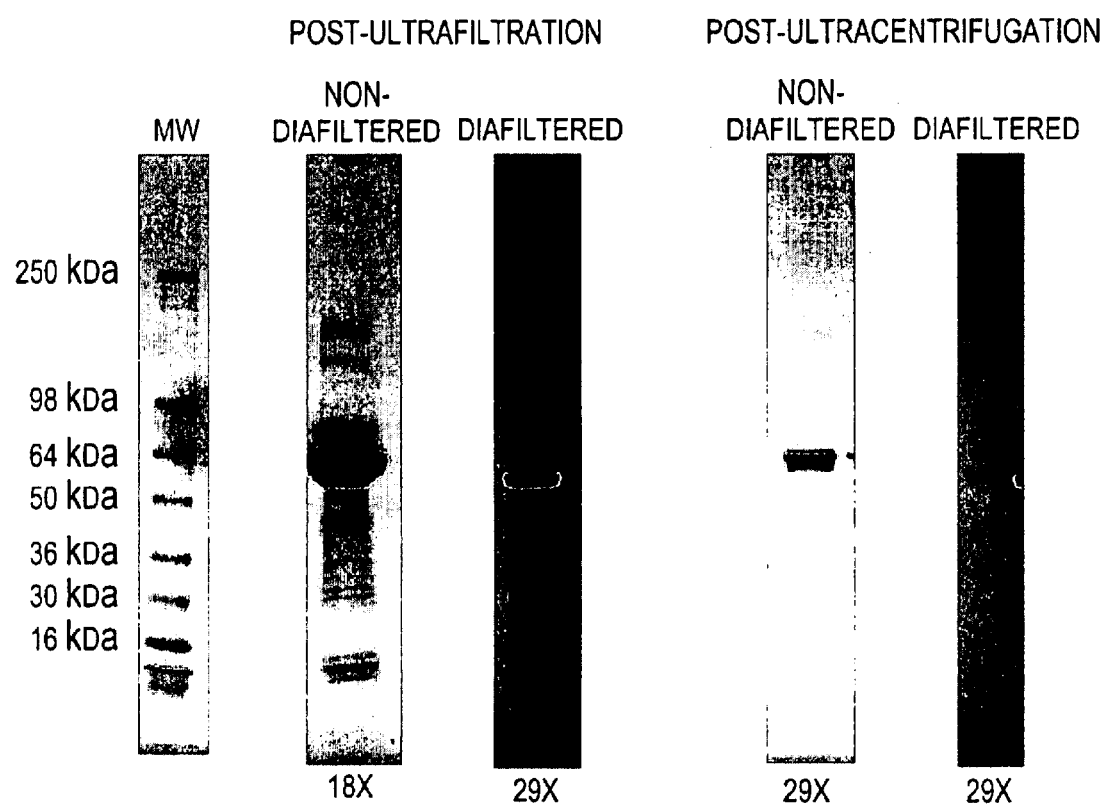

FIG. 7. SDS-PAGE of a concentrated tissue culture supernatant containing dexosomes prior to and after diafiltration with PBS with a 500 kDa hollow fiber membrane. The sample was diafiltered with 5 volumes of PBS. Pre- and post-diafiltered dexosomes were further purified by ultracentrifugation onto a density cushion composed of 30% sucrose/Tris D20 buffer. The fold concentration is depicted for each sample analyzed. 20 uL of the pellet (reducing conditions) was run on an 8–16% acrylamide gel that was subsequently stained with colloidal Coomassie Blue.

Figure 8A:
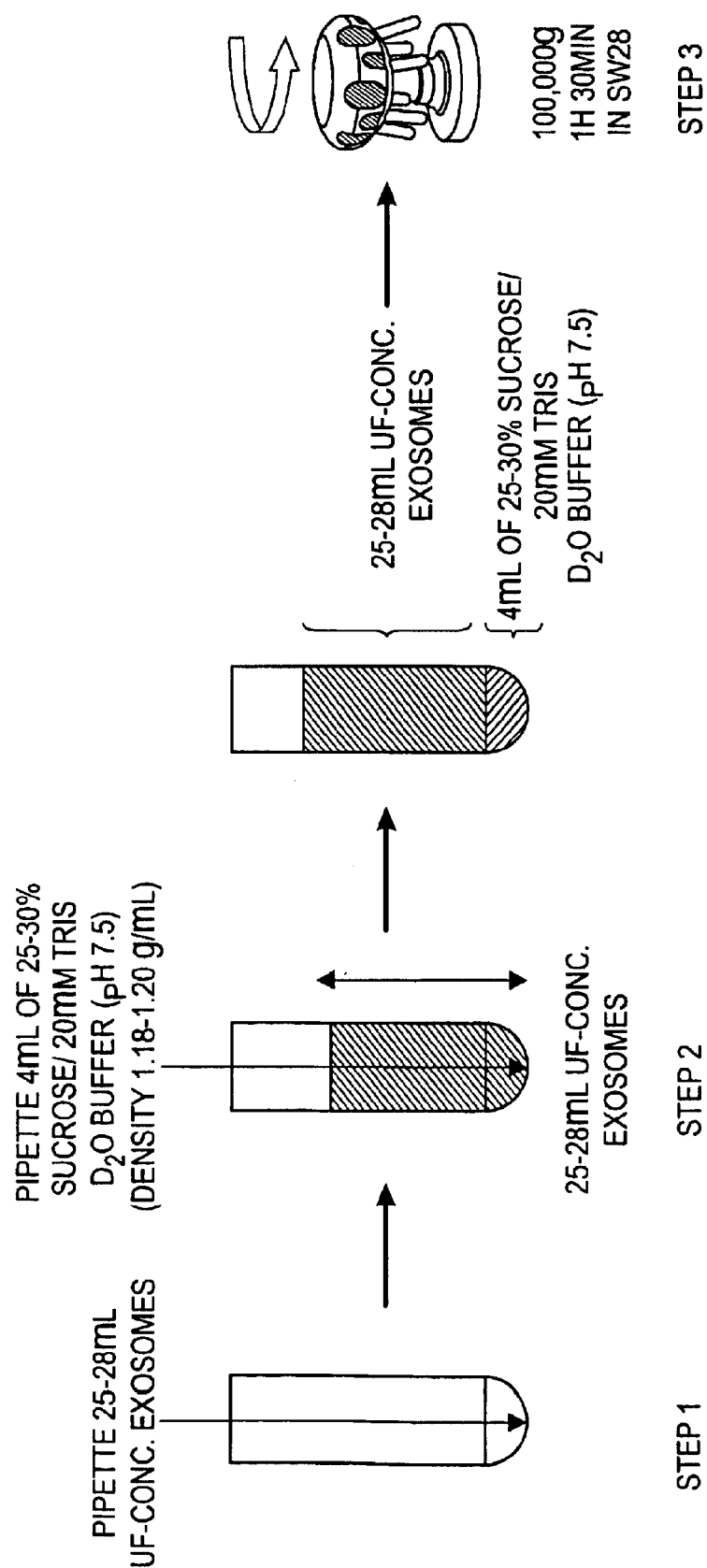

FIG. 8a. Ultracentrifugation of concentrated Dexosomes into a 30% sucrose/Tris $D_2O$ density cushion (density= 1.190–1.210 g/mL)—Sample Preparation FIG. 8b. Sample collection from Dexosomes ultracentrifuged onto a density cushion composed of 30% sucrose/Tris $D_2O$ buffer. The pellet is resuspended to $1/1000^{th}$ of its original volume with formulation buffer.

Figure 9A:
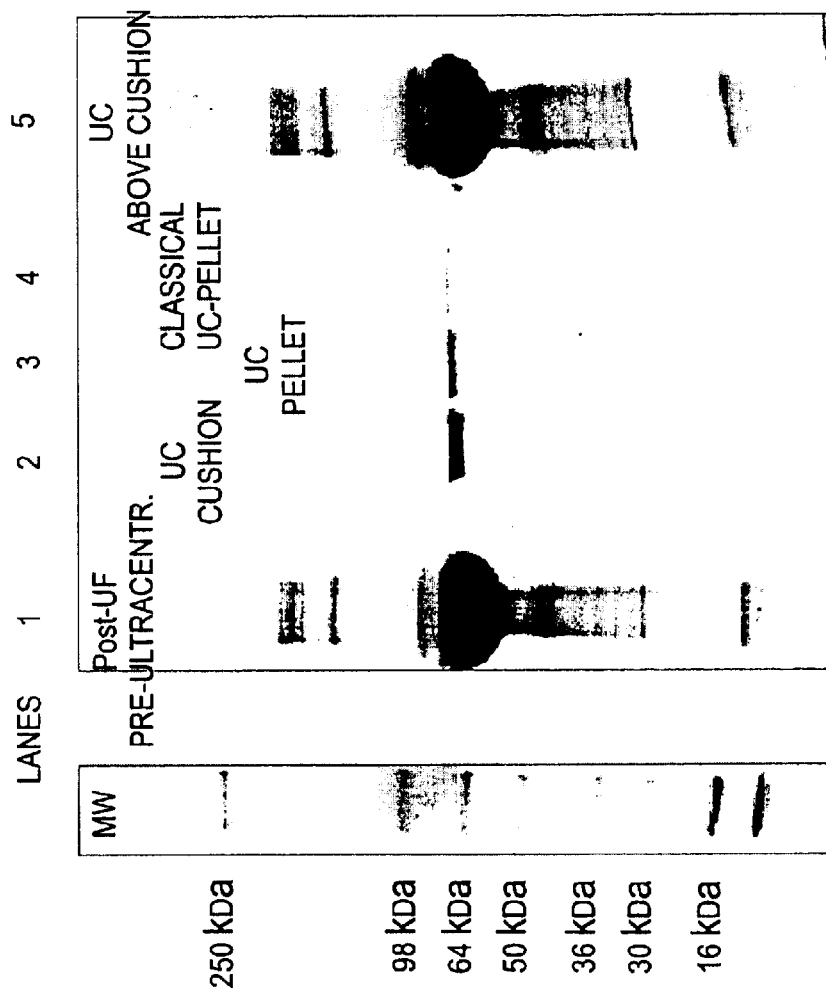

FIG. 9a. SDS-PAGE of dexosomes fraction collected after ultracentrifugation onto a density cushion composed of 30% sucrose/Tris D2O buffer. All samples were normalized to $1/21^{th}$ the original volume. Fractions were as follows: Lane 1Post-Ultrafiltration/Pre-Ultracentrifugation, Lane 2—UC density cushion fraction, Lane 3—UC pellet at bottom of cushion/reconstituted to $1/1000^{th}$ original volume, Lane 4—UC pellet obtained classical sedimentation method/reconstituted to $1/1000^{th}$ original volume, and Lane 5—UC above cushion.

FIG. 9b. HLA/DR ELISA of different fractions of the sucrose/D2O density cushion after ultracentrifugation at 100,000×g for 1 hour. No HLA/DR is observed above the cushion, approximately 10% of the signal in the reconstituted pellet ($1/1000^{th}$), and 90% in the cushion.

Figure 10:
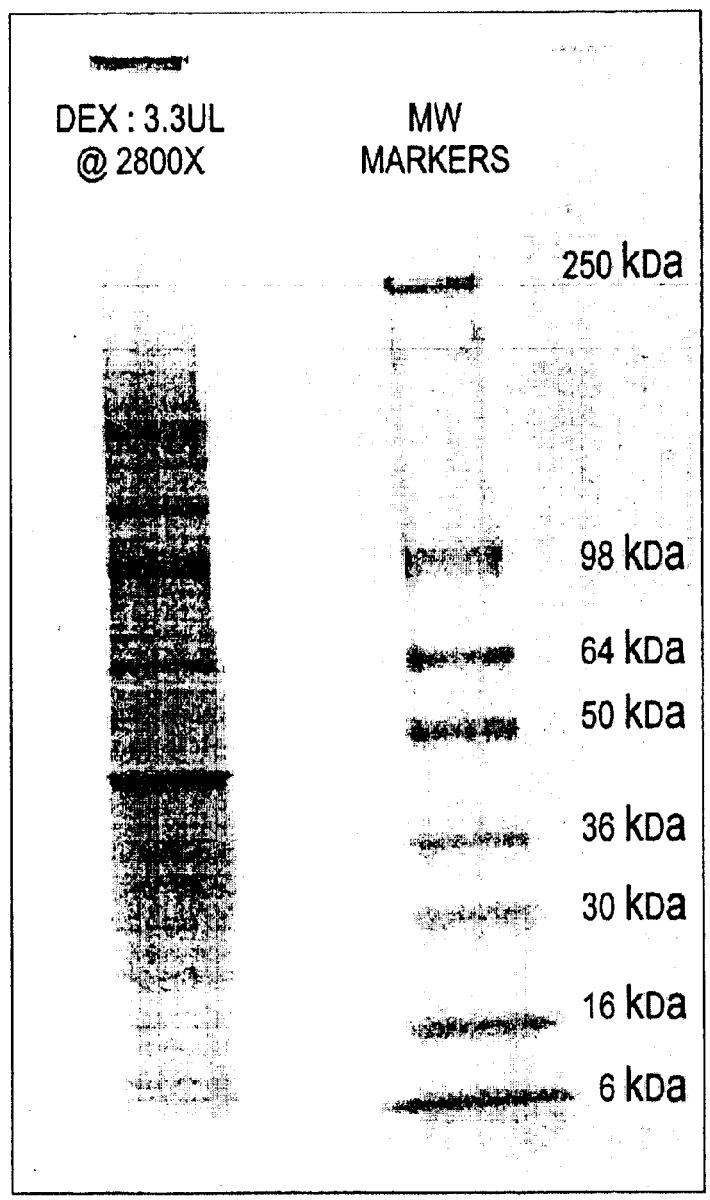

FIG. 10. SDS-PAGE of dexosomes and diafiltration into PBS formulation buffer. Dexosomes were concentrated further by sedimentation by ultracentrifugation at 100,000×g for 1hour. The pellet was reconstituted in PBS to $1/2800^{th}$ the starting supernatant volume. 3.3 uL of dexosomes (reducing conditions) was loaded onto a 8–16% acrylamide gel that was subsequently stained with colloidal Coomassie Blue.

FIG. 11. ELISA of Exosomes. Exosomes were purified by either pelleting by ultracentrifugation or by ultracentrifugation onto a density cushion solution (30% sucrose/20 mM Tris in D2O). For comparison, DC lysate was used at equivalent cell culture equivalents. Non-specific binding sites were blocked with nonfat dry milk and CD81 (FIG. 11a) and HLA-DR (FIG. 11b) were detected via specific mAb followed by detection with horseradish peroxidase conjugated secondary antibodies. Samples were quantitated by chemiluminescent detection and plotted as a function of cell culture equivalence.

FIG. 12. HLA/DR (FIG. 12a,b) and MHC I (FIG. 12c,d) ELISA of a Dexosome Preparation. Dexosome preparation was made by the methods described previously. Cell culture supernatant (3.7 L) was clarified by filtration, concentrated by ultrafiltration, concentrated by ultracentrifugation onto a sucrose/D2O density cushion, and concentrated with buffer exchange by ultrafiltration/diafiltration. The volume was normalized to represent a 1000× (1 uL equivalence=1 mL supernatant) concentration of the original supernatant volume.

Figure 12D:
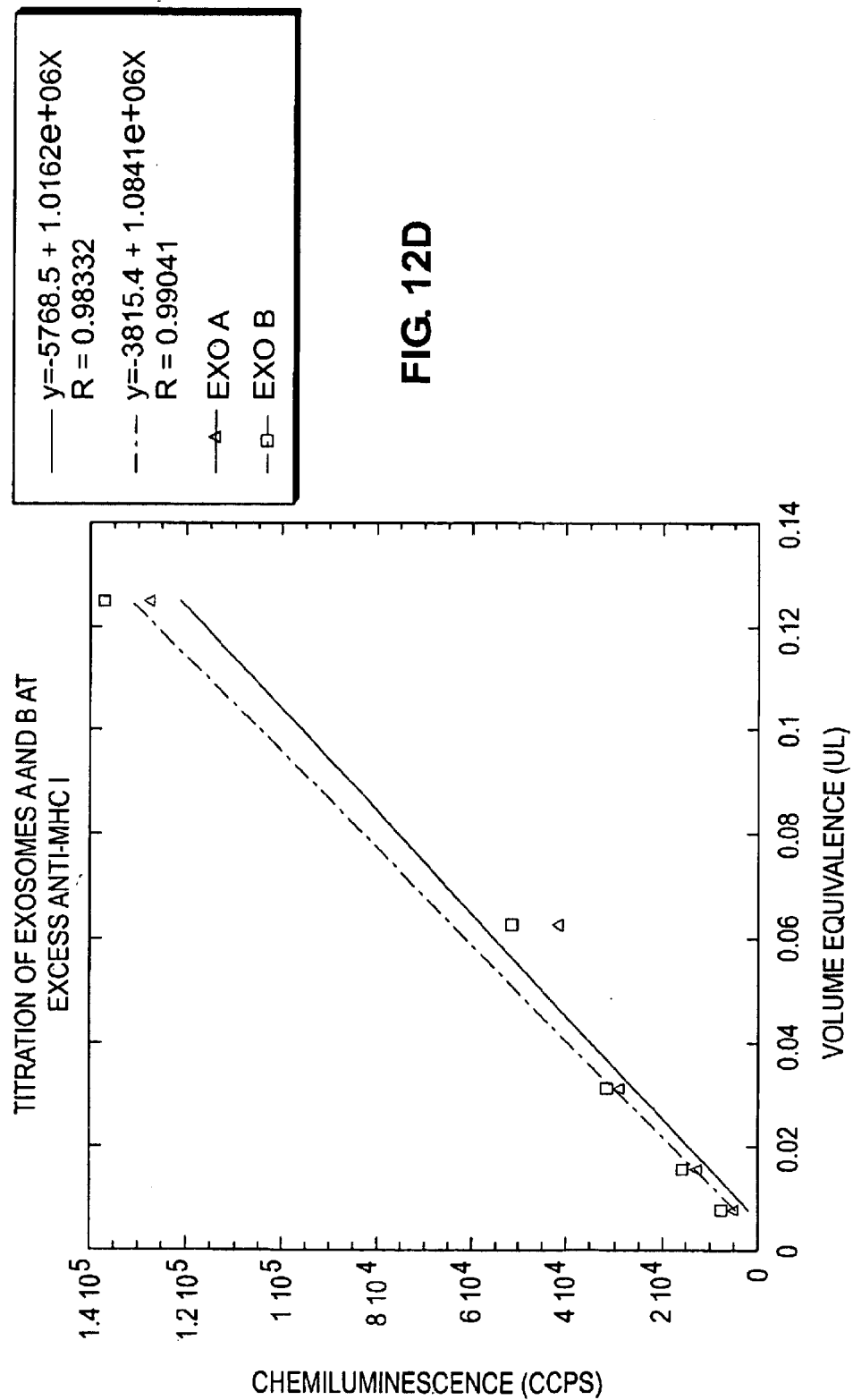
Figure 13A:
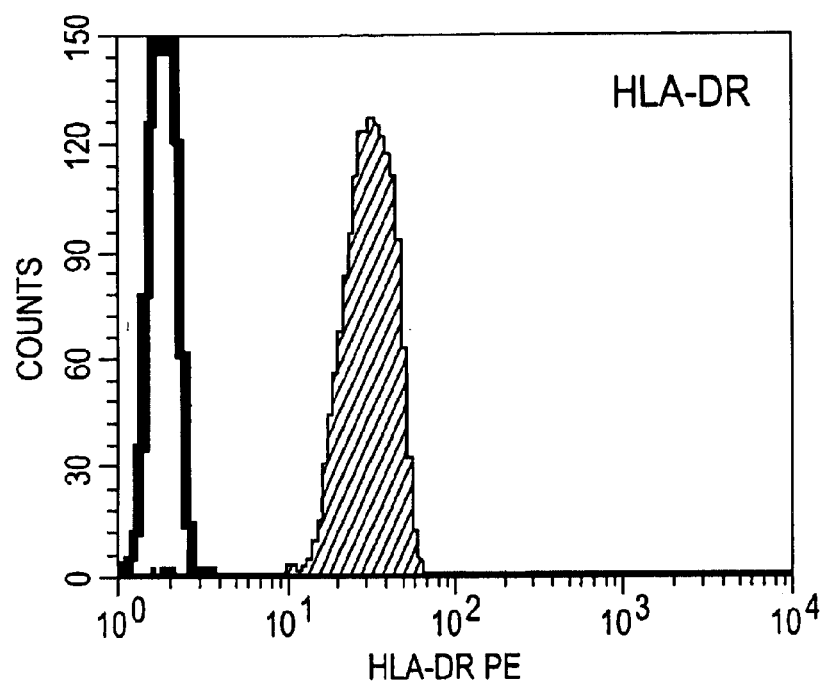
Figure 13B:
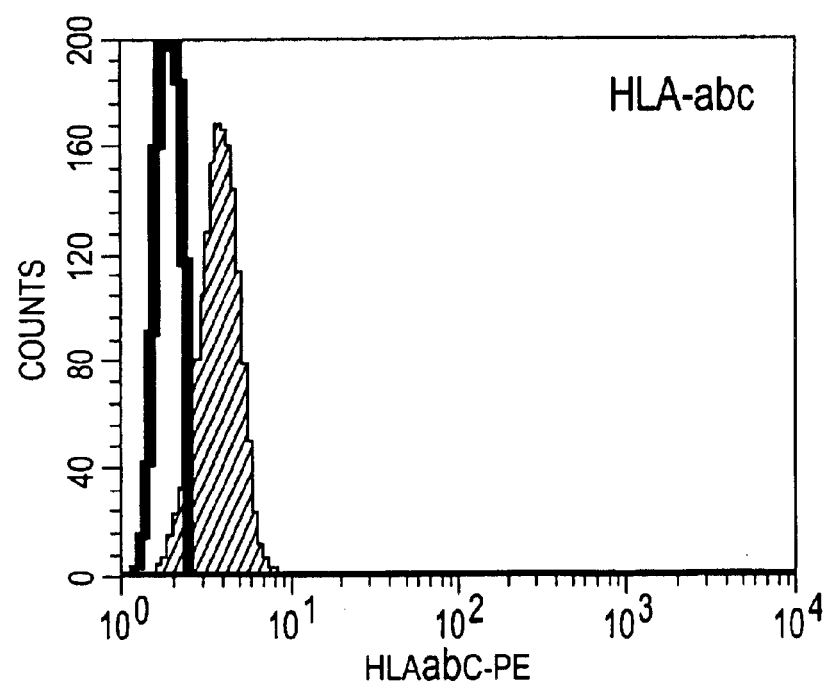
Figure 13C:
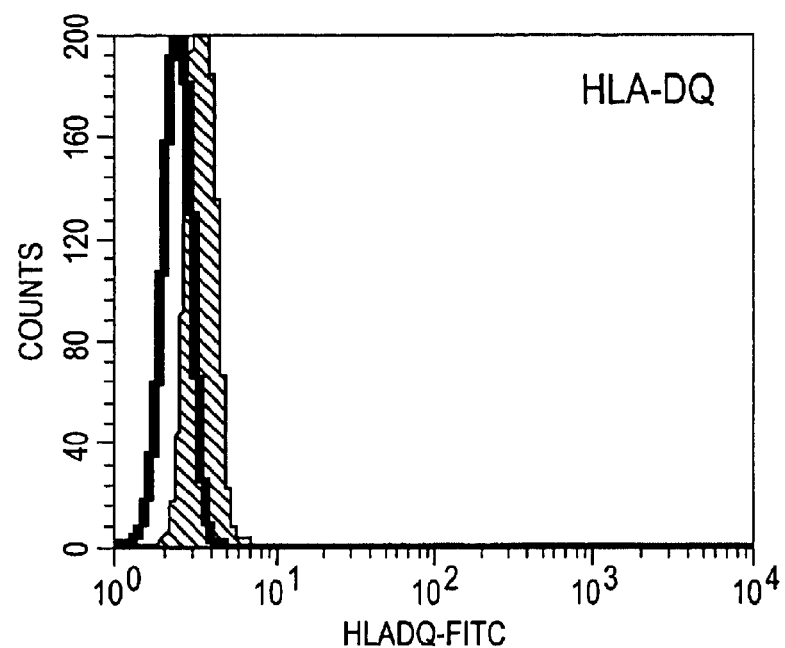
Figure 13D:
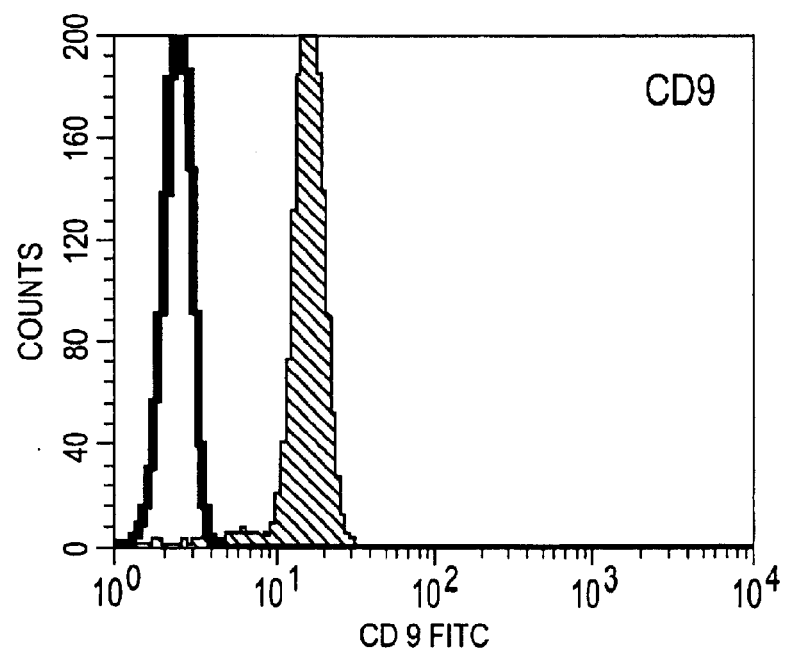
Figure 13E:
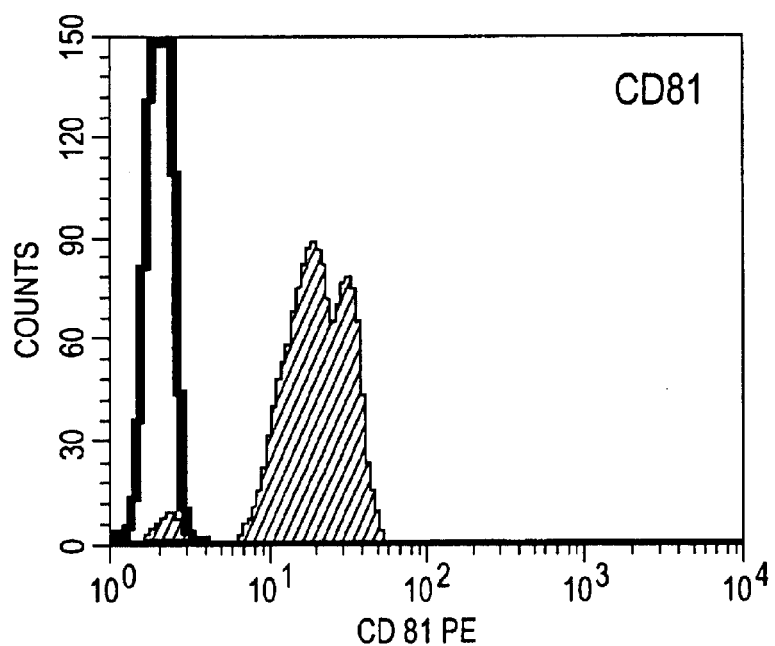
Figure 13F:
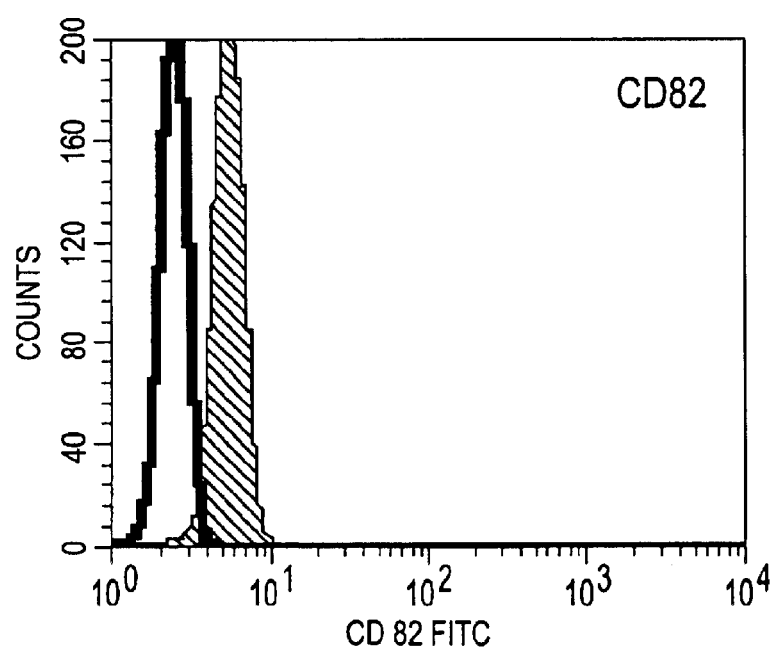
Figure 13G:
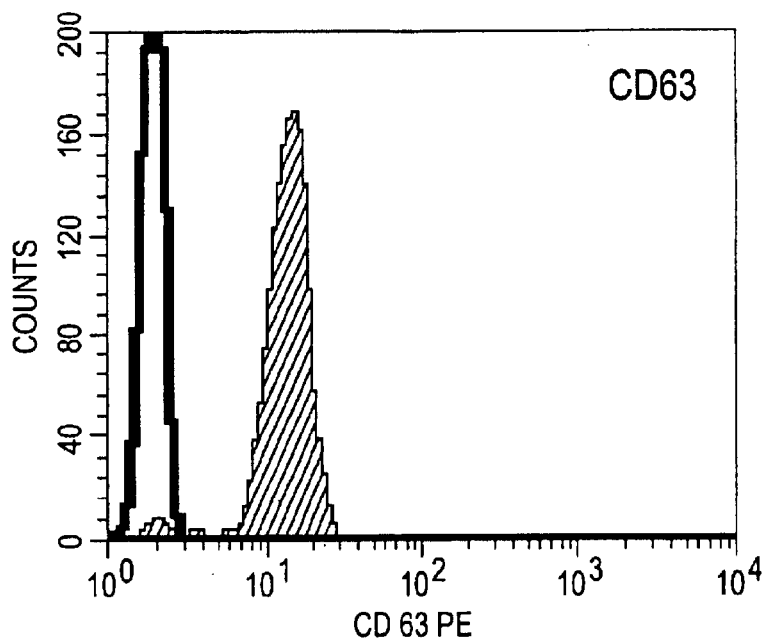
Figure 13H:
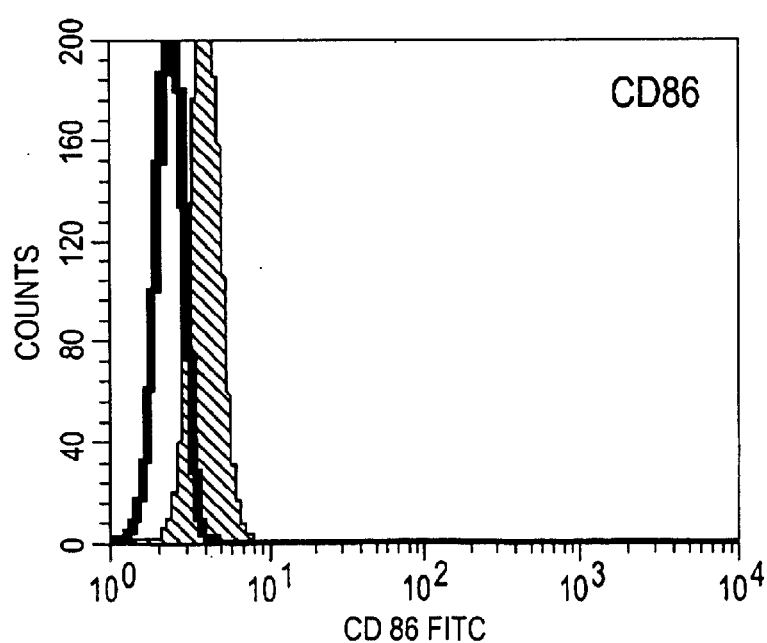
Figure 13I:
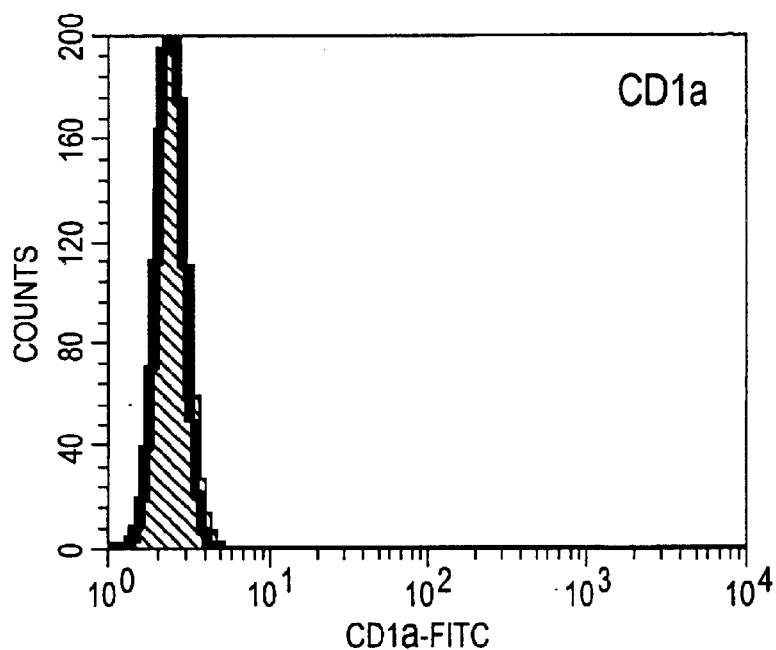
Figure 13J:
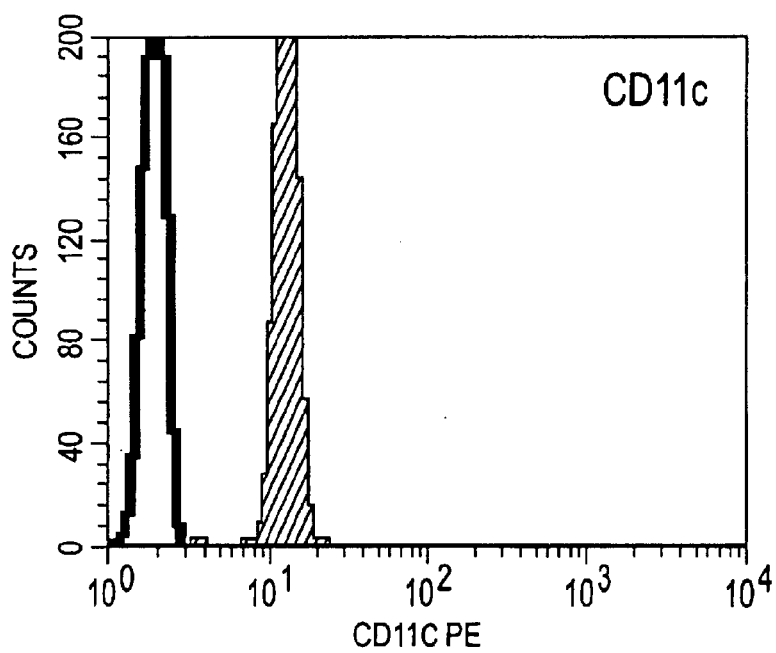
Figure 13K:
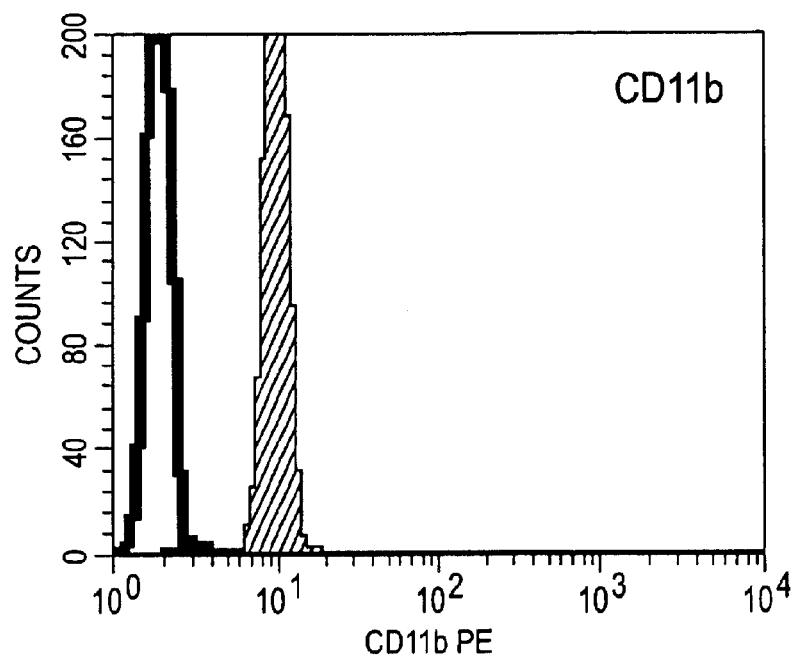
Figure 13L:
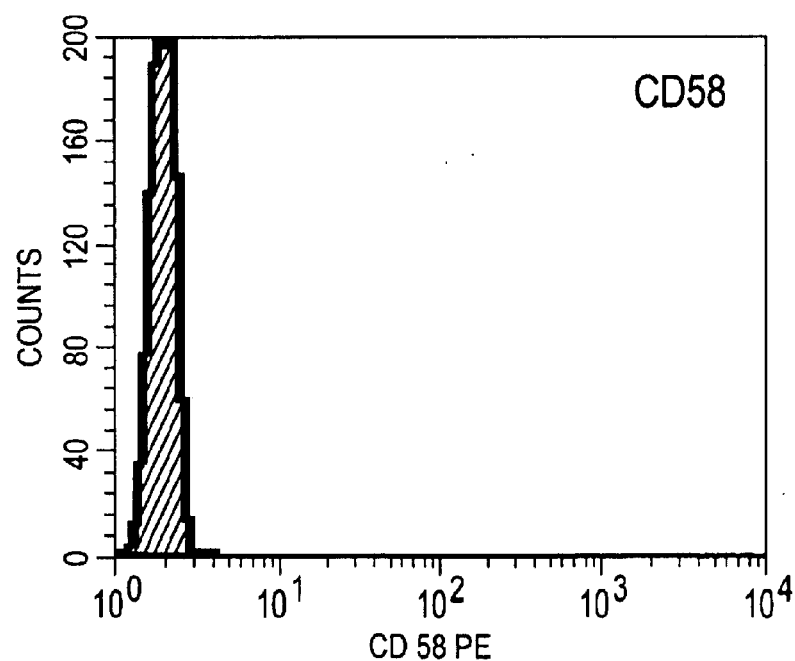
Figure 13M:
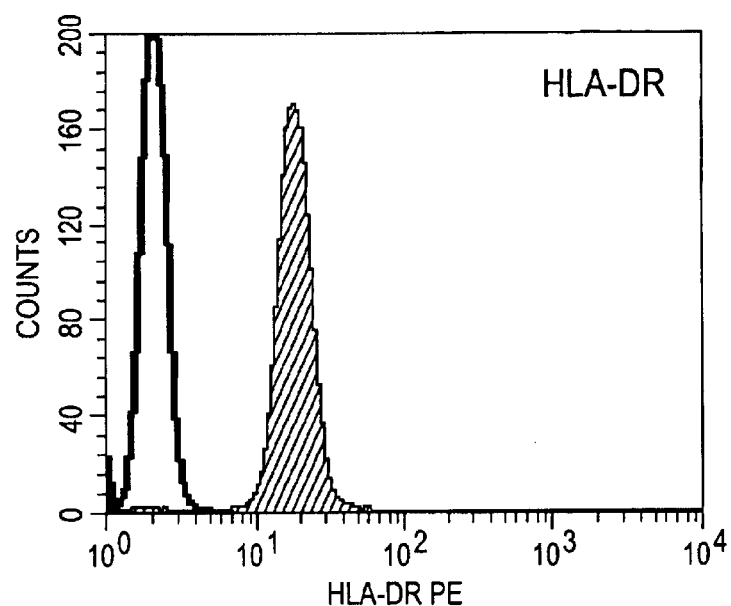
Figure 13N:
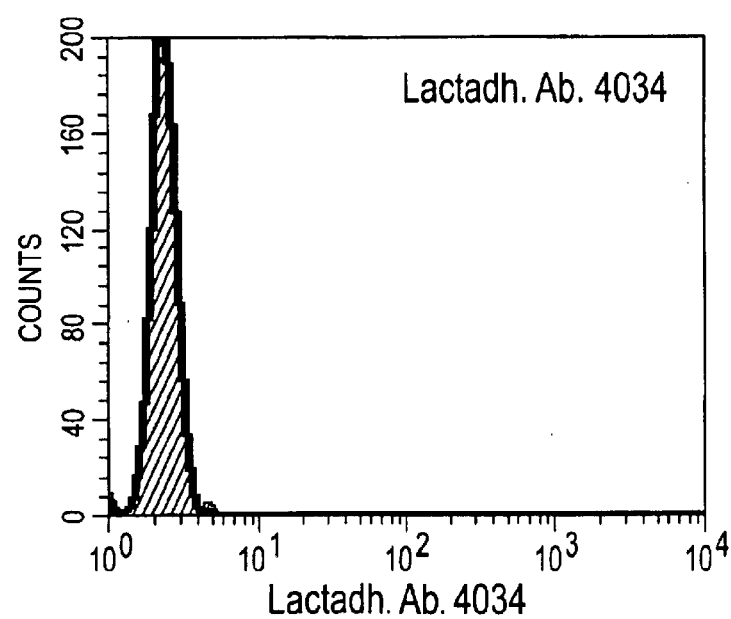
Figure 13O:
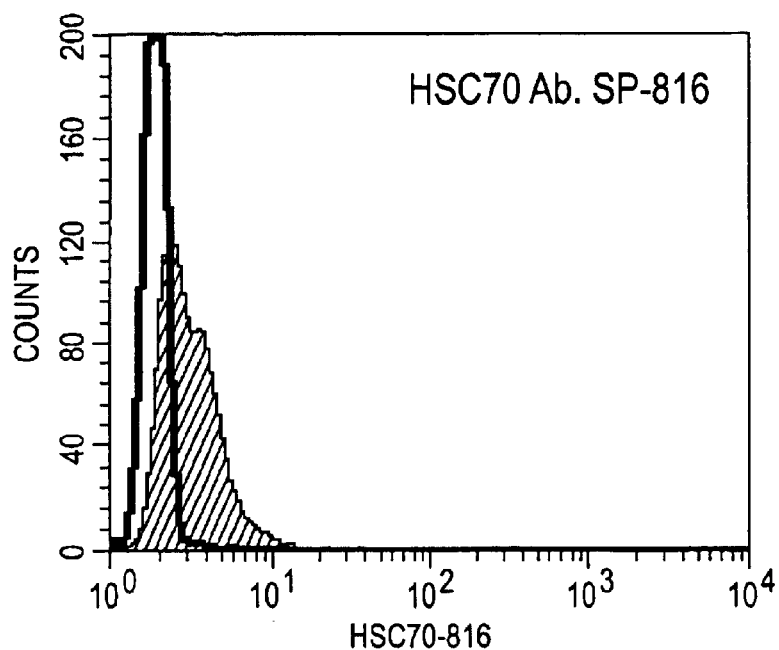
Figure 13P:
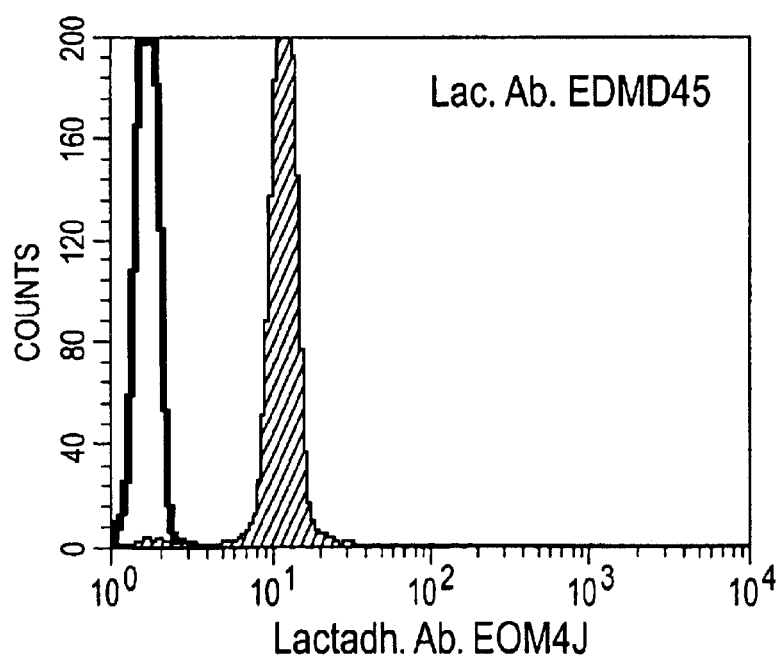

FIG. 12a. Titration of anti-HLA/DR with excess exosomes. FIG. 12b: Titration of dexosomes after ultracentrifugation into the cushion (UC-Cushion) and after diafiltration into formulation buffer (2nd UF) with excess anti-HLA/DR. FIG. 12c: Titration of anti-MHC I (HC-10 hybridoma) with excess dexosomes. FIG. 12d: Titration of dexosomes A and B with excess anti-MHC I.

FIG. 13. FIG. 13a: Flow cytometry analysis of Dexosomes for specific surface receptors. Shaded histograms illustrate specific intensity of binding of fluorescent labeled antibodies recognizing noted receptors and open histograms show irrelevant background binding. FIG. 13b. As for FIG. 13a except that staining was performed using unlabelled primary antibodies followed by fluorescent labeled secondary antibodies since lactadherin antibody is not available as direct fluorescent conjugate.

Figure 14:
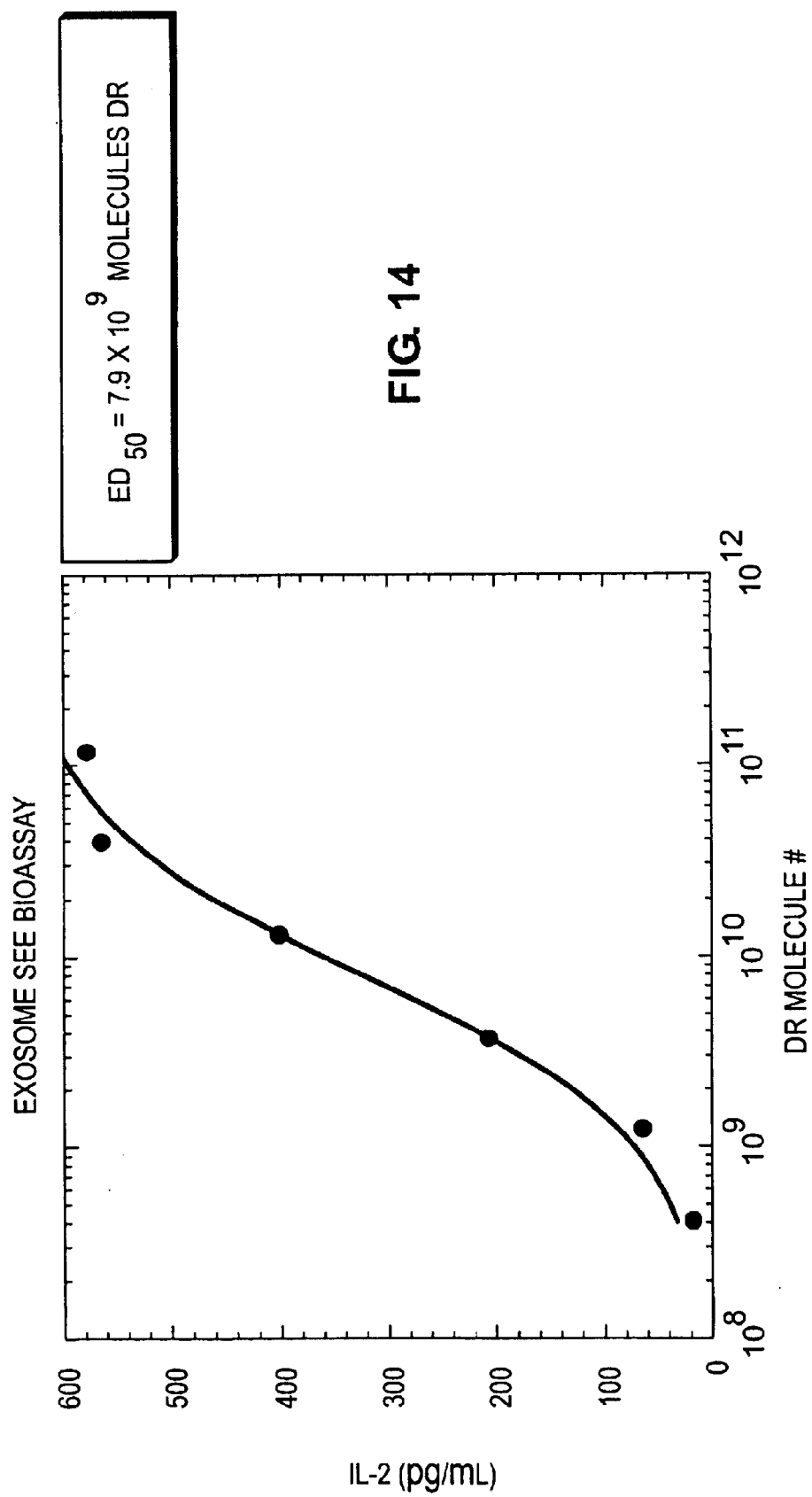

FIG. 14. Superantigen assay using SEE-pulsed dexosomes. Dexosomes were purified and pulsed with SEE as described in the examples, then incubated with a combination of Jurkat T cells and Raji cells. Production of IL-2 was measured by ELISA and plotted as a function of number of HLA-DR molecules per well as determined by HLA-DR ELISA assay. The data was fitted using a sigmoidal curve fit and a calculated half-mazimal effective dose (ED50) was derived as a measure of the potency of the dexosome preparation.

Figure 15:
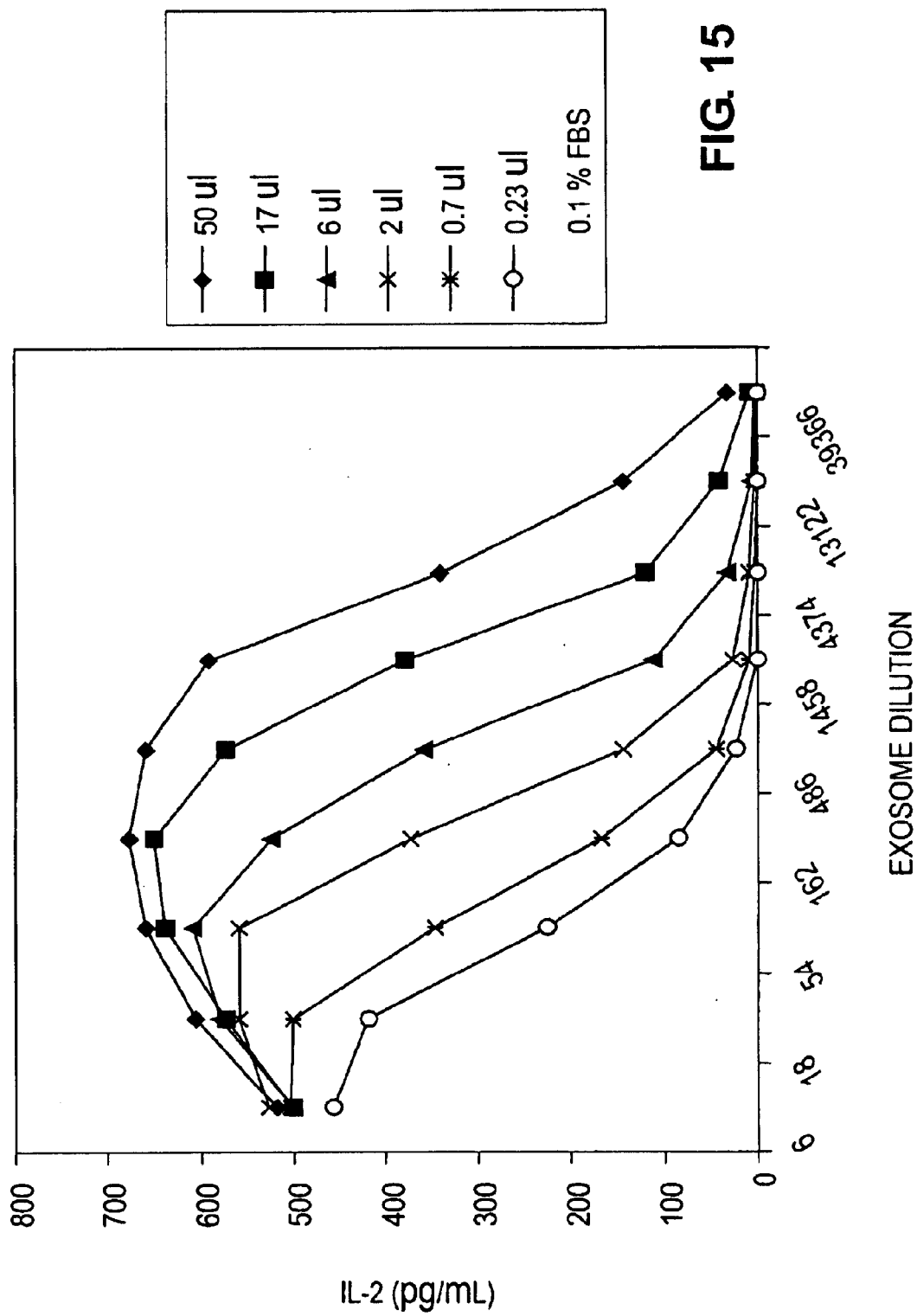

FIG. 15. Diluted quantities of dexosomes (shown in the legend) were pulsed with SEE and cultured with Jurkat and Raji cells to test the potency of the Dex preparations. After recovery from the Optiprep cushion, each sample was subjected to a serial titration and tested in the cell assay. The data show that after correcting for the dilution of each dexosome preparation, the same level of activity is registered if one views the region of the curves registering approximately half-maximal activity (approximately 350 pg/ml IL-2) for the range of 0.7 ul to 50 ul of exosomes representing a range of nearly 100-fold over which the assay is linear. This result is unexpected for such an assay and makes the assay very useful to measure a wide range of concentrations of unknown Dexosome preparations.

Figure 16:
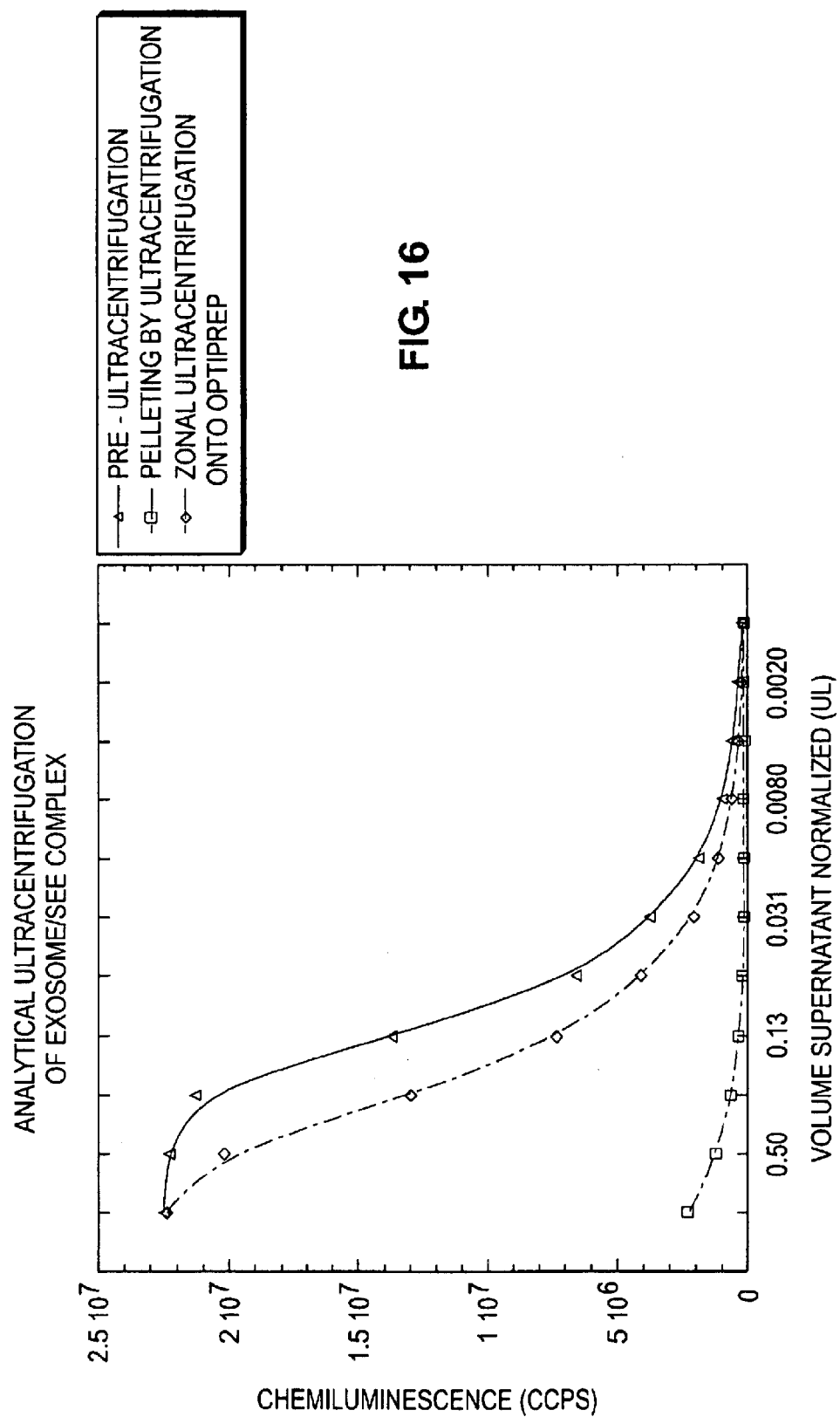

FIG. 16. HLA/DR ELISA comparison of exosome/SEE complex purified by pelleting and zonal ultracentrifugation.

DETAILED DESCRIPTION OF THE INVENTION

As indicated above, the present invention provides novel methods and compositions to prepare and/or characterize membrane vesicles, which are suitable for use in pharmaceutical domains, such as immunotherapy of various pathological conditions. This invention also discloses methods of removing haptoglobin aggregates from compositions such as media, biological products and the like, which can be used in various pharmaceutical or experimental areas.

Detailed description of the various steps that can be implemented to prepare membrane vesicles according to preferred specific embodiments of this invention will now be provided. It should be understood that the present invention is not limited to methods comprising all of these steps, but also include individual steps per se, as mentioned above.

A schematic representation of a complete process scheme for preparing membrane vesicles is depicted on FIG. 1. This general process comprises several main phases, including (i) the production of the (biological) sample containing membrane vesicles, (ii) the enrichment phase, (iii) the density cushion separation phase, (iv) the formulation and conditioning phase and (v) the quality control or characterization phase. Furthermore, the invention also describes methods of removing haptoglobin from biological materials such as culture media.

Haptoglobin Aggregates Removal

A particular and important aspect of the present invention resides in the provision of compositions that are essentially free of particulate bodies such as haptoglobin (and related polymers), more specifically of haptoblobin aggregates. In particular the present invention resides in the provision of cell culture media or biological products, such as proteins or polypeptides (or derivatives thereof) isolated from biological fluids (e.g., hSA compositions, gamma immunoglobulin, coagulation factors, serum, etc.) or buffer formulations, that are essentially free of aggregated haptoglobin.

Haptoglobin is a complex (alpha-beta)$_2$ tetrameric protein incorporating two types of alpha chains, alpha-1 (8.86 kDa) and alpha-2 (17.3 kDa), in various combination(s) It has been reported that haptoglobin can form large protein aggregates upon heat inactivation of serum products ("Biological Functions of Haptoglobin—New Pieces to an Old Puzzle" W. Dobryszycka, Eur. J. Clin. Chem. Biochem. 1997, 35(9), p.647–654; "Immunosuppressive Effect of Acute-Phase Reactant Proteins in vitro and its Relevance to Cancer", R. Samak et al., Cancer Immunol Immunother 1982, 13, p. 38–43). Furthermore, it is known that haptoglobin may exhibit immunogenic activity (Dobryszycka, supra, Oh et al., J. National Cancer Institute 1990, 82(11), p. 934–940). The present invention now recognizes the critical importance of haptoglobin aggregates that are present in many biological products and proposes new methods that allow the removal thereof.

More particularly, within the context of the present invention, haptoglobin aggregates designate any particulate body comprising a haptoglobin polypeptide or chain, more preferably cross-linked to any other polypeptide or protein through a S—S binding for instance, in particular any mixed aggregate of a haptoglobin polypeptide and albumin. Such haptoglobin aggregates may also comprise additional components such as hemopexin, transferring, Gc-Globulin and/or β$_2$-glycoprotein, as described by Jensen et al. (Vox Sang 67, 1994, 125).

While culture media are routinely used in both research and clinical applications, the issue of large soluble protein aggregates (or particulates) has not been addressed in the art, and their removal not suggested. The present invention now shows that the protein aggregates from AIM V co-purify with dexosomes upon pelleting via ultracentrifugation. Furthermore, this application shows that concentration of dexosomes generated in AIM V by ultrafiltration resulted in concentration of AIM V proteins. Furthermore, SDS-PAGE (FIG. 3) of concentrated dexosomes depicted 2 major bands at 42 kDa and 64 kDa corresponding to haptoglobin -chain and albumin.

This invention thus demonstrates that haptoglobin aggregates (including sub-units, cross-linked chains, aggregated forms, etc.) is found in conventional mammalian cell culture media. This invention further shows that haptoglobin aggregates are not removed by conventional exosome purification methods. The present invention now provides methods of removing particulate bodies, more preferably haptoglobin aggregates from biological materials such as culture media, biological compositions, buffering formulations, etc. The invention also discloses novel compositions of matter that are essentially deprived of haptoglobin aggregates and their uses. Removal (or reduction of the concentration) of large protein aggregates such as haptoglobin aggregates provides several significant advantages such as increased purity, increased safety, reduced non-specific immunosuppressive activity, etc. Furthermore, the invention discloses that aggregated haptoglobin-free culture media still allow an efficient cell culture and production of exosomes, while greatly enhancing the purification of the exosomes. Removal of protein aggregates from the media offers additional safeguards against the induction of undesirable immune responses to serum components such as haptoglobin (Dobryszycka, supra). In this regard, it is believed that haptoglobin aggregates can cause more undesirable immune response than non aggregated haptoglobin which is already known to be immunosuppressive (Se-Kyung Oh et al J. Natl Cancer Inst. 1990, 82, 934–940 Interference with immune response at the level of generating effector cells by tumor-associated haptoglobin). Protein aggregates are known to be 10,000 (ten thousand) times more immunogenic than soluble forms because they are preferentially captured by antigen presenting cells (M. Kovacsovics-Bankowski et al Proc Natl Acad Sci USA 1993, 90, 4942–4946 Efficient major histocompatibility complex class I presentation of exogenous antigen upon phagocytosis by macrophage). So, even present at very low dose, haptoglobin aggregates could be deleterious.

Furthermore, the methods of this invention also allow to remove other particulate bodies such as exosomes which may be present in serum-containing culture media. Removal of pre-existing exosomes further increases the purification of the products and avoids contamination by other immune-stimulating agents.

Method of Removal

Various methods can be used for removing particulate bodies (e.g., protein aggregates, more particularly haptoglobin aggregates) according to the present invention, such as (ultra)filtration, microfiltration, size exclusion chromatography (SEC), affinity chromatography, ion exchange chromatography, and ultracentrifugation. It may also be possible to remove the protein aggregates in the human serum component (i.e. Fraction V) by these methods prior to formulating with the medium.

In a preferred embodiment, the medium or composition is treated by ultrafiltration to remove protein aggregates or other particulate bodies, more specifically aggregated haptoglobin.

In a particular embodiment, ultrafiltration is performed using a 500 kDa hollow fiber membrane. This is the preferred molecular weight cutoff (MWCO) for this application since proteins such as transferring (approximately 75–80 kDa) are required to pass through the membrane. Measurements of transferring concentration by ELISA indicate that it quantitatively passes through this pore size. This membrane size retained the protein aggregates in the retentate while allowing the un-aggregated proteins to pass through with the permeate. The permeate is collected, sterile filtered through 0.22 $\mu$m filter into bottles, and stored at 4° C. until use.

While a 500 kDa MWCO hollow fiber membrane is preferred for ultrafiltration of culture media, other sizes of membrane may also be used such as 750 kDa, 300 kDa, 100 kDa, etc. Preferably, the medium is ultrafiltered with a membrane having a diameter comprised between 100 kDa and 1000 kDa, more preferably between 200 kDa and 750 kDa. In this respect, Applicants have now determined that 90% of haptoglobin aggregates present in culture media or other biological products such as heated serum albumin have a diameter comprised between about 40 nm and about 200 nm, as measured by dynamic light scattering. Accordingly, any membrane (or other separation device such as filters, hollow fibers, etc.) having a pore diameter below about 40 nm would be suitable and preferred for performing the present invention. As an illustration, a MWCO of 500 kDa represents a pore diameter comprised between about 20–25 nm.

Also, while the hollow fiber membrane format is the preferred embodiment for ultrafiltration, other types of ultrafiltration devices in a cassette for-mat (i.e. plate or frame cassette) may be used such as the Millipore Pelicon and related products, as well as cassettes from Sartorius Inc or Filtronics Inc. The membrane material is typically composed of polyether sulfone (PES), however other materials such as polypropylene may also be used.

In addition, a large range of operating parameters may be used in ultrafiltration of the media. Typical operating parameters are such that the inlet and outlet pressures are between 5–15 psi for optimal processing. A much lower or higher pressure may be used during processing.

In another specific embodiment, the medium is treated by microfiltration (0.05 µm, 0.1 µm, 0.21 µm, etc) to remove particulate bodies (e.g., protein aggregates). The preferred lumen diameter of the fiber is 0.5 mm, however other diameters such as 0.25 mm, 0.75 mm, and 1 mm may also be used.

These various treatments allow the production of media or biological products with reduced particulate bodies content, which have now been shown to significantly enhance the purification of the exosomes as well as the quality of the resulting preparation.

Aggregated Haptoglobin-free Media

In a particular aspect, the present invention thus resides in the use of pre-treated culture media, having a reduced particulate bodies content, as well as compositions of matter comprising such pre-treated media. Indeed, it has now been shown that pre-treatment of the media to reduce the content of particulate proteins (or protein aggregates) reduces significantly the contaminants present in the process, increases the efficacy of the method, allows the production of exosome preparations with higher purity and safety, and does not affect culture efficacy or cell viability.

Accordingly, in a particular embodiment of the present invention, membrane vesicles are prepared from biological samples produced by cells cultured in a culture medium with reduced particulate bodies (or protein aggregates) content.

Furthermore, another object of this invention resides in a method of producing dendritic cells, comprising culturing dendritic cell precursors in a medium comprising growth factors and/or cytokines to effect or stimulate differentiation of said precursors into dendritic cells, in particular into immature dendritic cells, wherein the medium has a reduced particulate bodies content, more preferably is essentially free of haptoglobin aggregates.

The invention also lies in a composition comprising dendritic cells (or any other membrane-vesicle producing cells) in a culture medium with reduce particulate bodies content such as haptoglobin aggregates, more specifically in a medium that is essentially free of aggregated haptoglobin.

The culture or production medium may be any medium suitable for culturing mammalian cells, in particular human cells. Examples of such media include AIM V, RPMI, DMEM, and the like, more generally any mammalian cell culture medium comprising proteins (or serum or substitute thereof). Preferred media include serum-free media, which are suitable for clinical uses.

The term "essentially free", "deprived of" or "reduced content in" haptoglobin aggregates indicates that the medium or product contains preferably less than 1 ppm of haptoglobin aggregates, more preferably less than 0.5 ppm by weight of aggregated haptoglobin. More particularly, the Applicants have now determined, by SDS PAGE and ELISA, that above 99% of haptoglobin aggregates could be removed from biological products such as AIM V media. More specifically, the culture medium is essentially devoid of particulate bodies (including protein aggregates, precipitates, and the like) having a diameter above 100 nm. In a further preferred embodiment, the medium is essentially devoid of particulate bodies (including protein aggregates, precipitates, and the like) that do not pass through a 500 kDa membrane. A more preferred culture medium of this invention is a culture medium that contains less than about 20 ng/ml, more preferably less than about 10 ng/ml of aggregated haptoglobin, as determined by ELISA (using for instance monoclonal antibody H6395 of Sigma). Furthermore, it should be noted that the presence of haptoglobin aggregates is generally not noticeable until the media is concentrated (by ultracentrifugation or ultrafiltration). A preferred media of this invention thus does not contain haptoglobin aggregates, as measured by SDS PAGE analysis and ELISA.

Aggregated Haptoglobin-free Biological Products

The invention is also suitable for the production of compositions of biological products (e.g., blood products) that are essentially free of aggregated haptoglobin, as well as to the treatment of various buffer solutions prior to formulating products for pharmaceutical uses.

In this respect, the present invention relates to a composition comprising a biological polypeptide or a derivative thereof, that is essentially deprived of haptoglobin aggregates. More particularly, this invention resides in a composition comprising a heat inactivated biological polypeptide that is essentially deprived of haptoglobin aggregates. The biological polypeptide may be any polypeptide, protein or peptide isolated (or extracted) from a mammalian biological fluid, in particular from blood, serum or plasma. Preferred examples of biological polypeptides include serum-albumin, gamma immunoglobulin, coagulation factors (e.g. factor VIII, factor IX), more preferably of human origin. The composition of the present invention are even more preferably characterized by containing less than about 0.01%, particularly less than about 0.001% haptoglobin aggregates.

In a specific example, this invention relates to a composition of heat inactivated serum-albumin, more preferably human serum-albumin, essentially free of aggregated haptoglobin. Purified hSA is widely used in the pharmaceutical industry (plasma complement, protein stabilizing agent, etc.). The presence of haptoglobin in hSA solution was demonstrated to be responsible for the formation of aggregates during heat treatment. Furthermore, aggregated proteins seem to be at least ten thousand times more immunogenic than un-aggregated forms thereof, so that their presence might be deleterious to the activity and safety of the preparation. The present invention now allows to remove any such haptoglobin aggregate from hSA preparations, more particularly through ultrafiltration as described above, thereby providing novel hSA compositions with high purity and quality for pharmaceutical uses. More particularly, the invention now provides hSA preparations that contain less than about 0.01% by weight (wt) of aggregated haptoglobin, even more preferably less than about 0.001% wt. The specific examples described in this application demonstrate that albumin preparations containing about 0.00025% wt aggregated haptoglobin, or less, may be obtained with the present invention. More preferably, the albumin preparations (or compositions) of this invention are heated hSA preparations (or compositions), especially for pharmaceutical uses.

The invention also resides in a method of treating a biological product, more preferably a heat inactivated biological product, in order to reduce the amount of haptoglobin aggregates contained therein, the method comprising subjecting the product to filtration, more preferably ultrafiltration.

A particular object of this invention also resides in a method of preparing a biological product comprising (i) a heat inactivation of the biological product and (ii) a filtration of the heat inactivated biological product. More preferably, the method further comprises the step of (iii) concentrating the filtered, heat inactivated biological product and/or (iv) the conditioning thereof. The method can be used for various biological products including any protein or polypeptide (or derivatives thereof) isolated (or extracted) from mammalian biological fluids such as human blood or plasma or serum. As will be further documented in this application, this method allows, for the first time, the production of heat inactivated biological products having a reduced content in haptoglobin aggregates, more preferably essentially free of haptoglobin aggregates and thus with increased safety. The method is particularly suited for the preparation of pharmaceutical proteins extracted from blood or plasma such as serum-albumin, more preferably a human serum-albumin, gamma immunoglobulin, coagulation factors, etc. The filtration step comprises preferably an ultrafiltration, even more preferably with a MWCO comprised between about 100 kDa and about 1000 kDa, typically between 200 kDa and 750 kDa. The filtration may be conducted in any device and condition as disclosed above. Furthermore, alternative methods as described above may also be used.

In this regard, the invention also relates to methods of treating albumin preparations comprising subjecting an albumin preparation to filtration, preferably ultrafiltration. A more preferred method resides in the treatment of a heated hSA composition (or preparation) by ultrafiltration on a porous device having a mean pore diameter comprised between 200 kDa and 750 kDa. Because of the large amounts of hSA used in the pharmaceutical area, Applicants' method and compositions of higher quality represent significant advantage in terms of security.

Production of the Sample

As indicated above, the current invention relates to the production of membrane vesicles and is suitable to prepare membrane vesicles from various origins, including membrane vesicles produced by antigen-presenting cells (such as macrophages, dendritic cells, B lymphocytes), tumor cells or any other cell or cell line producing membrane vesicles. It is particularly suited for preparing membrane vesicles produced by dendritic cells, preferably immature dendritic cells (i.e., dexosomes). Furthermore, the membrane vesicles or corresponding producing cells can be sensitized to one or several antigens, prior to, during or after preparation.

Monocyte Cell Culture

Various methods of producing biological samples containing dexosomes or other membrane vesicles have been disclosed in WO99/03499, incorporated therein by reference.

A preferred methodology within the scope of this invention is based on the production of dendritic cells ("DC") from monocyte precursors or bone marrow, more preferably immature DC. Indeed, the inventors have shown that immature DC have the capacity to produce exosomes, while mature DC essentially fail to do so. More specifically, within the scope of this invention, it is preferred to use compositions of immature dendritic cells obtained by treating monocyte precursors (contained in blood or marrow) in the presence of a combination of cytokines, more preferably in the absence of DC maturation factor or condition, and/or for a period of time that does not allow DC maturation.

Compositions of immature dendritic cells preferably comprise essentially (i.e. at least 60%, preferably 70%) immature dendritic cells.

Therefore, the dendritic cell preparation step advantageously comprises the preparation of a composition of immature dendritic cells, particularly of human origin, especially from monocyte precursors, more specifically by treatment with a combination of cytokines such as GM-CSF+ IL-4 or GM-CSF+IL-13, in the absence of maturation factors and/or in serum-free media to avoid maturation.

In addition, within the scope of this invention, it is also possible to use immortalised dendritic cell populations. These may consist of immortalized dendritic cell lines (e.g. D1 line or any other line produced by introducing the myconcogene in the dendritic cells, for example). They may also consist of dendritic cells prepared and immortalized in vitro. The interest of immortalized dendritic cells lies in the constitution of banks of cells sensitised to given antigen groups, which may be used industrially to prepare dexosomes compatible for administration to entire families of patients.

To produce the membrane vesicles (dexosomes), the immature dendritic cell population may be simply cultured under conventional conditions known to those skilled in the field. However, it is preferred to culture these cells under conditions stimulating the production of dexosomes, particularly in the presence of factors capable of stimulating dexosome production, particularly a cytokine such as gamma interferon, interleukin 10 or interleukin 12 (e.g. see application WO99/03499). In a preferred embodiment of the process according to the invention, the immature dendritic cell population is cultured under conditions stimulating membrane vesicle production. Preliminary experiments indicate addition of interferon gamma enhances the efficacy of dexosomes in vivo in preclinical mouse tumor models. On day 7, the media is collected for subsequent dexosome isolation.

In a specific embodiment of this invention, the patients' peripheral blood samples are cultured in clinical grade AIM V, a serum-free cell culture medium (Life Technologies, Inc). Prior to use, the culture medium undergoes ultrafiltration to remove aggregated proteins (e.g., haptoglobin), whose removal was shown by applicants not to affect cell growth, but aids considerably in the subsequent isolation of pure dexosomes.

It is understood that membrane-vesicles can be prepared by any other means and used in the present invention. In particular, membrane vesicles may be produced artificially, or with immortalized cell lines or obtained from previously established collections or banks.

Sensitization of the Cells or Vesicles: Antigen Loading

The membrane vesicle-producing cells (e.g., dendritic cells) can be sensitized to an antigen prior to (or during) membrane vesicle production. Alternatively, the membrane vesicles themselves may be sensitised. This embodiment allows the production of vesicles with a given immunogenicity. The sensitisation may be performed using different well-known techniques, comprising for example placing the cells (or vesicles) in contact with antigenic peptides, antigens, protein complexes, cells or membranes of cells expressing antigens, apoptotic bodies, membrane vesicles, liposomes, tumoral RNA or any nucleic acid coding for one or more antigens, antigenic determinants or epitopes (possibly carried by a viral or non-viral vector), etc. (e.g. see application WO99/03499). In a preferred method, the sensitisation is performed by incubation of the producing cells with peptides, antigens, RNA or nucleic acids. It is understood that this application is not limited to sensitisation or production techniques.

Many antigens can be used to sensitize dendritic cells (or membrane vesicles), by exposure of the cells (or vesicles) to said antigens, corresponding proteins, peptides, nucleic acids and the like. Preferred antigens are tumor antigens, viral antigens, bacterial antigens and the like. Typical tumor antigens include melanoma antigens (MAGE, MART, BAGE, etc), prostate-specific antigens (e.g. PSMA), CEA, ras, p53, Rb, liver tumor antigens, etc.

Protein antigens are processed inside dendritic cells ("DC") to specific peptides, which are then captured by the MHC molecules for presentation at the cell surface. For a given protein, human DC of different HLA haplotypes present different peptides (epitopes). Relevant peptides can be loaded to the MHC class I of DC by incubating DC and peptides under the proper conditions. It is also possible to load antigens directly on the isolated dexosomes in vitro. In a specific example, MAGE-A3 and -A4 peptides comprising known epitopes for HLA-A2 are synthesized for use in loading the patients' dexosomes. Inclusion criteria for patient in this experiment include expression of the HLA-A2 haplotype. The HLA A2$^+$ haplotype is relatively frequent, being present in approximately 50% of the human population.

Furthermore, control antigens such as TT (tetanus toxoid) and CMV peptides can also be added, in particular the TT P2 peptide. The purpose of the control antigens is to serve as an internal control to test the function of dexosome in antigen presentation with known antigens. Therefore, as a positive control, dexosomes are also loaded for instance with the CMV peptide (class I) and TT P2 peptide (class II). A positive response with these controls indicates that the dexosomes are active. CMV has the advantage of providing a test for both the initial and recall antigen response because approximately 50% of the general population are immune to CMV (recall) and the remainder is naïve (initial).

Example 3 below describes preliminary results obtained in a model system for the loading and assay of CMV peptide (antigen) on dendritic cells and dexosomes. The results demonstrate the ability of loaded vesicles to stimulate antigen-specific CTLs (FIG. 2).

It should be understood that any other sensitization method and antigen(s) may be used in the current invention, to confer desired immunogenic properties to the membrane vesicles.

Enrichment of the Sample

As indicated above, the sample (e.g. supernatant, lysate, biological fluid, etc.) may be subjected to an enrichment step, which may comprise one or more centrifugation, clarification, ultrafiltration, nanofiltration, affinity chromatography and/or diafiltration steps. In a specific embodiment, the enrichment step comprises (i) the elimination of cells and/or cell debris (clarification), possibly followed by (ii) a concentration and/or diafiltration step. A preferred enrichment step according to this invention comprises (i) the elimination of cells and/or cell debris (clarification), (ii) a concentration, and (iii) diafiltration.

Clarification of the Sample

The cells and/or cell debris may be eliminated by centrifugation of the sample, for example, at a low speed, preferably below 1000 g, between 100 and 700 g, for example. Preferred centrifugation conditions during this step are approximately 300 g or 600 g for a period between 1 and 15 minutes, for example.

Preferably, the cells and/or cell debris are eliminated by filtration of the sample, possibly combined with the centrifugation described above. The filtration may particularly be performed with successive filtrations using filters with a decreasing porosity. For this purpose, filters with a porosity above 0.2 μm, e.g. between 0.2 and 10 μm, are preferentially used. It is particularly possible to use a succession of filters with a porosity of 10 μm, 1 μm, 0.5 μm followed by 0.22 μm.

Cell culture media is filtered by microfiltration through a disposable 0.8 μm capsule filter composed of cellulose acetate to remove cells and debris. The microfiltration capsule is single use. A scheme of the process is shown in FIG. 5. A minimum of 10 experiments indicate that the capacity of the microfilter, e.g. 500 cm$^2$ surface area, is sufficient for filtering dendritic cell culture supernatant of 2.5 liters to greater than 4 liters. If necessary a larger surface area (e.g. 1000 cm$^2$) may be used depending upon the amount of debris in suspension.

Other pore sizes 2 μm, 1 μm, 0.65 μm, 0.45 μm, etc may also be used to clarify cells and cell debris from the dexosomes. The microfilter may contain a pre-filter, i.e. the 0.8 μm Sartoclean Calif. (Sartorius Inc.) contains a 3.0 μm cellulose acetate pre-filter. Furthermore, the filter may be composed of other materials besides cellulose acetate such as polypropylene or polyether sulfone (PES).

Other methods that may be used for the removal of cells and debris from dexosomes are low speed centrifugation, continuous flow microfiltration through hollow fibers, and chromatography.

Concentration

A concentration step may be performed, in order to reduce the volumes of sample to be treated during the density cushion stage. In this way, the concentration may be obtained by centrifugation of the sample at high speeds, e.g. between 10,000 and 100,000 g, to cause the sedimentation of the membrane vesicles. This may consist of a series of differential centrifugations, with the last centrifugation performed at approximately 70,000 g. The membrane vesicles in the pellet obtained may be taken up with a smaller volume and in a suitable buffer for the subsequent steps of the process.

The concentration step is preferentially performed by ultrafiltration. According to a preferred embodiment, the (clarified) biological sample (e.g., the supernatant) is subjected to an ultrafiltration, preferably a tangential ultrafiltration. Tangential ultrafiltration consists of concentrating and fractionating a solution between two compartments (filtrate and retentate), separated by membranes of determined cut-off thresholds. The separation is carried out by applying a flow in the retentate compartment and a transmembrane pressure between this compartment and the filtrate compartment. Different systems may be used to perform the ultrafiltration, such as spiral membranes (Millipore, Amicon), flat membranes or hollow fibres (Amicon, Millipore, Sartorius, Pall, GF, Sepracor). Within the scope of the invention, the use of membranes with a cut-off threshold below 1000 kDa, preferably between 300 kDa and 1000 kDa, or even more preferably between 300 kDa and 500 kDa, is advantageous.

In a specific embodiment, the clarified tissue culture supernatant (e.g., obtained after clarification through a 0.8 μm filter) is concentrated by ultrafiltration through a 500 kDa molecular weight cutoff (MWCO) hollow fiber membrane having a lumen diameter of 0.5 mm (A/G Technology Inc). This pore size of the cartridge retains dexosomes in the retentate while allowing proteins that are smaller than the pore size to pass through the membrane. The hollow fiber cartridge contains sufficient surface area to allow the concentration to proceed rapidly without an excess of shear forces on the dexosomes. Typical volume of the starting supernatant that undergoes ultrafiltration is 2–4 L, which is then reduced to approximately 100 mL (20- to 40-fold reduction). The operation setup is depicted in FIG. 6.

Other pore sizes such as 30 kDa, 100 kDa, 300 kDa, and 750 kDa may also be used to concentrate the dexosomes volume. However, the process efficiency and percent recover may be reduced. Furthermore, other ultrafiltration formats such as the "plate and frame" cassettes from companies such as Millipore, Sartorius, and Filtronics may be used. Stirred cells such as those provided by Amicon Inc may also be used to reduce the volume of dexosomes.

The concentration of dexosomes by ultrafiltration by hollow fiber membranes proceeds under low shear forces. The shear force of the feed stream (e.g. flow rate <300 mL/min for 0.7 sq. ft. surface area) is less than 2000 $sec^{-1}$. The inlet and outlet pressures of the system are between 3–8 psi during the process. More stringent conditions may be used to concentrate dexosomes compared to the parameters currently used.

Other techniques such as ion exchange and affinity chromatography, as well as flow field-flow fractionation may also be used to concentrate dexosomes in the preparation method of this invention.

Diafiltration

Diafiltration of concentrated dexosome preparation can be employed to reduce the concentration of contaminating media and cellular proteins. Diafiltration may be performed according to several techniques allowing to exchange the sample buffer with formulation buffer, including ultrafiltration, chromatography, ultracentrifugation, and via a dialysis bag.

In a preferred embodiment, diafiltration is performed with an ultrafiltration system. As demonstrated in the experimental section, this embodiment is efficient. Furthermore, where the vesicle preparation has been concentrated by ultrafiltration, the diafiltration step may be combined easily therewith, using the same methodology.

In this respect, in a particular embodiment, the exosomes are diafiltered by ultrafiltration using the same ultrafiltration membrane (i.e. 500 kDa MWCO hollow fiber membrane) as used in the concentration step. This embodiment is advantageous since both steps can be performed essentially in the same device with limited intervention and manipulation of the exosomes, i.e., by mere modification of the products introduced into the hollow fiber.

Besides the 500 kDa hollow fiber membrane, other pore sizes such as 30 kDa, 100 kDa, 300 kDa, and 750 kDa, can be utilized, preferably comprised between 30 and 1000 kDa, more preferably between 200 and 750 kDa. The diafiltration buffer may be composed of excipients other than those found in PBS. The volume of buffer used in diafiltration may be anywhere from 1 to 10 times the volume of the dexosome concentrate.

Operation parameters used for diafiltration are similar to those described previously for the concentration of dexosomes from clarified tissue culture media.

Density Cushion Separation and Purification of Exosomes

Figure 8B:
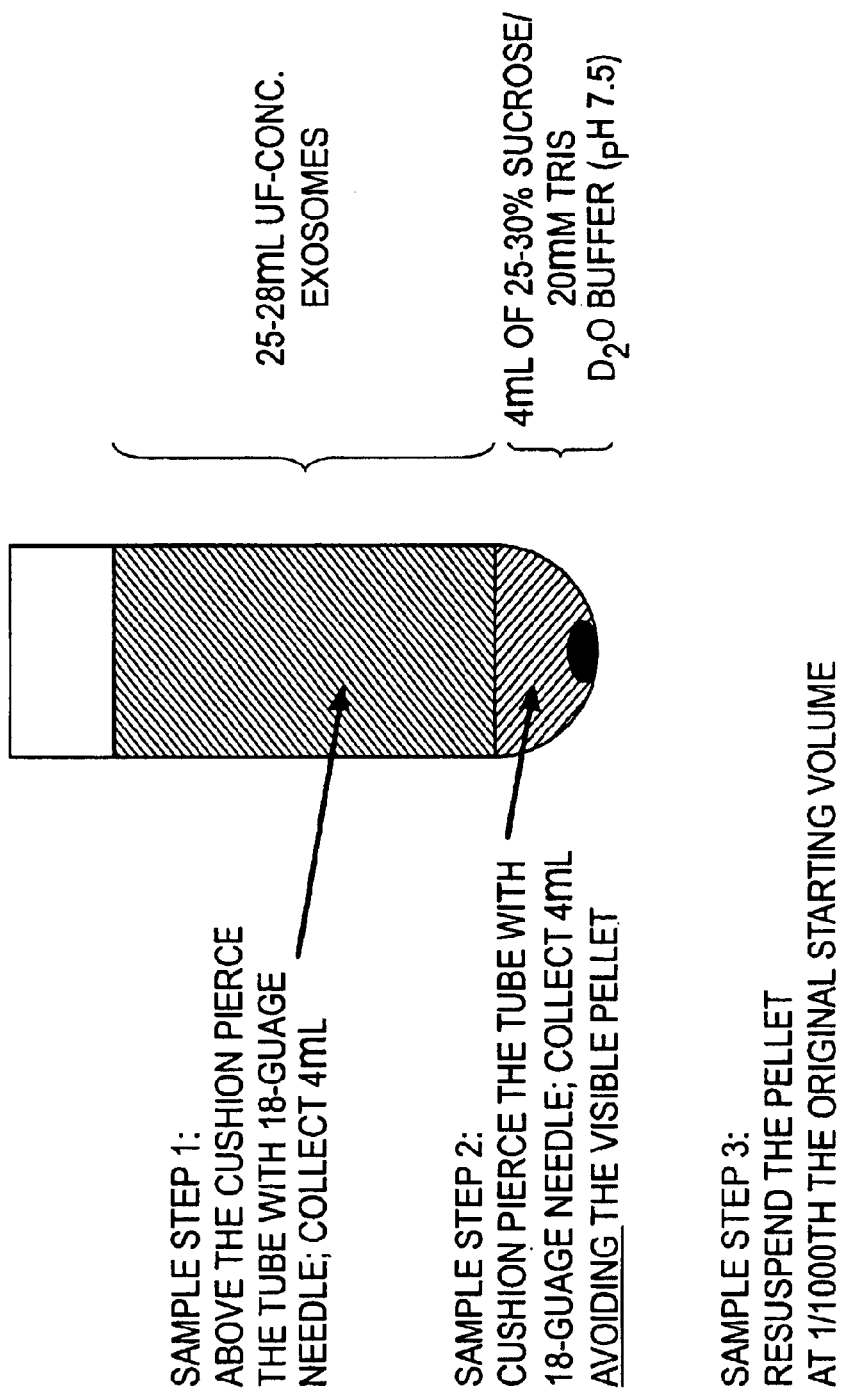

As indicated, the present invention discloses the treatment of a biological sample comprising membrane vesicles by centrifugation on density cushion, and the recovery of the purified vesicles from the cushion. Density cushion centrifugation provides several advantages over prior art techniques using serial centrifugation or gradient density centrifugation. These include, lack of aggregation of the vesicles which are thus subjected to reduced physical injury, further purification of the vesicles, since additional contaminants can be removed, as will be discussed below, lack of toxicity of the components used in the cushion, reduced sucrose concentration, etc. In particular, the density cushion allows to prevent pelleting of exosomes as the sample is ultracentrifuged. The difference in partial specific volume of soluble protein (about 0.73), exosomes (about 0.88) and protein aggregates makes this an ideal method for separation and purification. Protein aggregates (density about 1.35) are expected to pellet through the density cushion as the exosomes are retained in the density cushion. Briefly, the method is described as follows (a schematic of this process is depicted in FIG. 8a and 8b).

The addition of a higher density solution (i.e. cushion) to the bottom of the centrifuge tube compared to the concentrated dexosome solution results in the formation of a discontinuous or step gradient (i.e. sharp changes in density). The cushion results in exclusion of molecules of lower sedimentation coefficients. Furthermore, the cushion makes it easier to resuspend any sedimented material at the conclusion of the run, and prevents damage to particles that may not withstand pelleting.

Moreover, as another advantage, it is believed that the density cushion allows to further eliminate any potential contaminating protein aggregate, in particular haptoglobin aggregates, from the composition.

Membrane vesicles, in particular dexosomes, have been shown to have a density of 1.100 to 1.140 g/mL. Accordingly, the density cushion should have a final density of between about 1.10 and about 1.15.

The composition of the cushion may be adapted by the skilled person, so as to reach the above preferred final density. The cushion solution is preferably slightly hyperosmotic, with osmolarity between 700–800 mOs. In a preferred embodiment, the density cushion consists of sucrose/$D_2O$ in Tris buffer. The addition of the dense sucrose/Tris $D_2O$ buffer into the bottom of each tube displaces the concentrated dexosome solution upwards forming a visible interface. Ultracentrifugation at 100,000×g for approximately one and one-half hour sediments the dexosomes into the more dense sucrose/Tris $D_2O$ cushion. The dense cushion contains an enriched and more purified dexosomes population. Very few dexosomes are either above the cushion or in the pellet that sometimes is visible at the bottom of the tube. Furthermore, $D_2O$ has previously been used in the clinical setting and has not shown any toxicity effects in the concentrations that are being used. In this regard, the natural abundance of deuterium in humans is 15 mg/kg (0.15% wt).

Preferably, where a $D_2O$/sucrose cushion is used, the density of the initial cushion solution should range between about 1.175–1.210 g/mL (deviation from these specific limits can be used as well). Indeed, Applicants now have evidence that diffusion of $D_2O$/sucrose occurs in the cushion during centrifugation, leading to the formation of a mini-gradient and a final density between about 1.1 and about 1.15 g/ml (i.e. the density of the pooled cushion was measured to be between 1.100 and 1.150 g/mL). This was not expected and provides further advantages to the purification step since, by forming a mini-gradient, the cushion allows further purification of exosomes.

In other instance, other solutions besides sucrose/$D_2O$ may be prepared where the density of the solution is greater than that of the exosomes. In this regard, doubly-labelled water (i.e., $D_2^{17}O$ or $D_2^{18}O$) may be used, that would even allow to further reduce the amount of sucrose in the cushion. Density of available $D2^{18}O$ (97% pure) is 1.22. Mixture of $D_2O$ and $D_2^{17}O$ or $D_2^{18}O$ could be used to isolate vesicles and cellular fractions of various density without added component.

Higher concentrations of sucrose in $H_2O$ (non-deuterated) may also be prepared to generate a solution of comparable density, although such a solution would be significantly more hyperosmotic and may induce lysis of dexosomes.

Commercial density media composed of iodixanol (i.e. OptiPrep), Percoll, and Ficoll may be used to capture dexosomes in a similar fashion, for laboratory process and analytical purpose.

The purified exosomes can be collected from the cushion by any appropriate means, including piercing the tube with a needle, pipetting and the like.

Formulation and Conditioning

Formulation of Exosomes by Diafiltration

Purified exosomes can be formulated in various buffer or suspension suitable for clinical use or further storage.

For that purpose, purified exosomes can undergo buffer exchange by diafiltration with a 500 kDa ultrafiltration hollow fiber cartridge identical in format to that used previously for concentration and/or diafiltration (see previous discussion). The cartridge is preferably pre-conditioned with a buffer containing hSA (e.g. 100 ug/mL) that is void of haptoglobin contamination for a minimum of 15 min prior to diafiltration. It appears that the presence of hSA prevents non-specific loss of dexosomes due to binding to the hollow fiber substrate. The ultracentrifuge cushion fractions (approximately 16 mL) containing purified (antigen pulsed) exosomes undergo a minimum of 5 volume buffer exchange to remove the cushion components (i.e. a minimum of 98% buffer exchange). An identical setup to that depicted in FIG. 5 is used, however the hollow fiber cartridge is sized down to accommodate the smaller volume. As described previously, diafiltration is performed with low shear forces (i.e. 2000 sec$^{-1}$) which may not be necessary.

A typical SDS-PAGE of a dexosome sample at $\frac{1}{2800}^{th}$ its original volume is depicted in FIG. 10.

Several formulation buffers can be used to formulate exosomes. A typical buffer contains USP/NF excipients. The formulation solution may contain the following components: 1) a buffering agent such as Tris, 2) a cryoprotectant such as sucrose, trealose, glucose, glycerol, etc., 3) salts such as NaCl, KCl, MgCl$_2$, CaCl$_2$, etc., 4) bulking agents such as mannitol, glycine, starch, etc., 5) antioxidants, 6) vitamins, 7) stabilizing proteins and peptides such as hSA, and 8) other widely accepted excipients used in formulation.

In this regard, an object of the present invention resides in a composition comprising (i) membrane vesicles, (ii) a buffering agent and (iii) a cryoprotectant or a stabilizing compound. The composition preferably further comprises (iv) salts and/or bulking agent and/or antioxidants and/or vitamins.

Typical buffers comprise PBS, 20 mM Tris/5% sucrose/1 mM MgCl$_2$ pH 7.4, or 20 mM Tris/5% sucrose/1 mM MgCl$_2$ 100 ug/mL hSA pH 7.4 and are subjected to ultrafiltration to remove haptoglobin.

Preferably, the formulation solution as described above is essentially free of haptoglobin (or related polymers, as well as particulate bodies). In this regard, the formulation solution (or particular individual components thereof such as the albumin solution) may be subjected to ultrafiltration to eliminate haptoglobin as disclosed before. This final treatment further provides assurance of higher quality of the product.

Sterile Filtration and Freezing of Exosomes

Finally, the material collected (or formulated) may be subjected to further treatment(s) and/or filtration stages, particularly for sterilization purposes. In this regard, exosomes may be sterile filtered through filters with a diameter less than or equal to 0.3 µm. A typical sterilization comprises filtration through a 0.221 µm syringe filter (25 mm) with minimal loss (see HLA/DR assay results). Filters composed of Millipore's "Durapore" material can been used in sterile filtration. Other filter materials composed of cellulose acetate or polyether sulfone may also been used. The syringe filters are preferably pre-wetted with the formulation buffer containing 100 ug/mL hSA (minus haptoglobin) prior to filtering the exosomes. The exosome sample (~16 mL) may be sterile filtered either under controlled parameters with a syringe pump or by hand induced pressure.

The purified exosomes (optionally formulated and/or sterilized) may also be frozen and stored at −80° C., or other storage temperatures of −20° C. or 4° C. Freezing is preferably performed at a control rate of 1° /min with a "Mr. Frosty" cryo −1° C. freezing container (Nalgene Inc). Other methods of slow, or rapid freezing in liquid N$_2$ may also be employed.

In this regard, an object of this invention also resides in a composition comprising frozen exosomes.

Quality Control

The present invention also discloses and provides novel compositions and methods that can be used to characterize membrane vesicle preparations that have been prepared (e.g., purified and/or formulated), or during the preparation process. The compositions and methods of this invention can be used to evaluate the quantity of exosomes in a sample or a composition, to determine the phenotype of an exosome preparation and to assess the biological activity of an exosome preparation. These methods are particularly suited for characterizing a product for use in clinical applications, i.e., to control the quality and composition of an exosome preparation. These methods are very important for therapeutic purposes since essentially autologous (i.e., patient per patient) vesicle preparations are used, which require individual characterization parameters. These compositions and methods can be used to characterize exosome preparations from various origins (i.e., antigen-presenting cells, tumor cells, etc.), antigen-sensitivity (antigen-loaded, antigen-free, etc.), freshly prepared or stored, from primary cells or immortalized cell lines, etc.

Dosing of Exosomes

A method was developed to assess the quantity of membrane vesicles present in a sample (or a purified composition). The method involves immune complex formation and detection, using antibodies that recognize cell surface markers present on exosomes.

More specifically, the method of dosing membrane vesicles in a sample according to the present invention comprises (i) adsorbing the sample onto a solid support, (ii) contacting the adsorbed support with a (capture) antibody specific for a cell surface marker of exosomes and (iii) determining (or dosing) the presence of antibody-antigen immune complexes.

More preferably, the antibody specific for a cell surface marker of exosomes is an anti-class II antibody, i.e. an antibody that binds MHC Class II molecules, or an anti-class I antibody. Furthermore, in particular embodiments, at least a second capture antibody is used, in parallel, to further increase the selectivity of the assay with regard to exosomes. For instance, preferred additional capture antibodies are directed against the CD81 cell surface marker or against MHC class I molecules. The use of an anti-CD81 antibody is advantageous for characterizing (dosing) dexosomes since CD81 is significantly reduced from dendritic cells, and thus provides a signal that is specific to dexosomes. Other antibodies specific to exosomes may be used in this step, such as anti-CD63 or anti-CD9, for instance.

In a preferred embodiment, the exosomes are thus adsorbed onto a solid support and contacted separately with an anti-class II antibody and with an anti-CD81 antibody.

The antibody-antigen immune complexes formed as a result of the contacting step can be detected according to conventional immunological techniques. Preferably, the complexes are revealed using a labeled revelation antibody that binds the first and/or second capture antibodies. The revelation antibody may be labeled with radioactivity, enzymatic activity, fluorescent label, chemunilescent label, etc. The measure of the complexes correlates with (i.e., provides direct indication of) the quantity of exosomes present in the sample. Where two antibodies are used (e.g., anti-Class II and anti-CD81), an average or a ratio of the complexes detected with each antibody may be performed as a quantification parameter.

The various antibodies to be used in the method can be monoclonal or polyclonal antibodies, either in natural form or modified (e.g., humanized), fragments or derivatives thereof. In typical experiments, the capture antibodies are monoclonal antibodies. In a further typical experiment, the revelation antibody is a labeled monoclonal or polyclonal antibody.

In performing the present method, various solid supports may be used, such as a multi wells plate, in particular a 96-wells plate or any other titration plate.

Furthermore, in performing the current dosing method, it is highly-preferred to use purified exosome samples in order to reduce non-specific background signal. For that purpose, the sample is preferably a purified exosome sample, even more preferably a sample subjected to density cushion (ultra)centrifugation. For analytical purpose, a few ml of exosome solution is centrifugated on a $D_2O$ sucrose density cushion of 200 µl. The ELISA can be performed directly on the cushion solution. This simple purification step allows enough concentration and purification. The recovery is close to 100%.

In a specific embodiment, ELISA-based analyses have been developed in order to provide a quantitative measure of exosomes in a sample, composition, fluid, etc. FIG. 11a illustrates the measurement of HLA-DR (i.e. MHC II) and FIG. 11b illustrates the measurement of CD81 in dexosomes. The HLA/DR assay is both sensitive and functionally relevant to the activity of dexosomes, since HLA/DR is involved in antigen presentation. This assay was chosen as the quantitation assay for dexosomes preparation. The ELISA assay for HLA/DR determination quantifies dexosomes in the final product. Since this assay can also measure HLA/DR on dendritic cells, this assay provides a means for relating HLA/DR dose per dendritic cell and per volume of isolated dexosome.

Phenotyping of Exosomes

A method was developed to assess the phenotype of membrane vesicles present in a sample (or a purified composition). The method involves immune complex formation and detection, using antibodies that recognize several cell (surface) markers present on (in) exosomes. The method further comprises complexing the exosomes onto solid support such as beads, to allow a sensible and reliable determination of the phenotype of each preparation.

In this regard, an object of the present invention resides in a method of characterizing vesicle membranes in a preparation, comprising contacting, in parallel, samples of the membrane vesicle preparation with two or more antibodies specific for marker of the vesicles and determining the formation of antigen-antibody immune complexes.

The method is more specifically directed at determining the phenotype of an exosome preparation, i.e., the specific type of cell surface markers expressed by the exosomes in the preparation. Considering the autologous nature of exosome preparations, the phenotype is essential in characterizing the composition of the preparation, both in terms of structure and in terms of potential activity.

More preferably, the method of characterizing the preparation comprises an initial step of binding the exosomes onto solid supports, such as beads. Even more preferably, the exosomes are covalently attached to solid supports such as beads, or through antibody-mediated affinity binding. In a typical embodiment, beads with a diameter of about 1 to 10 µm, more preferably 3 to 5 µm are used and can carry above 1000 exosomes covalently attached thereto or coupled by immunoaffinity, more preferably between 2000 and 5000 exosomes. The exosome-coated beads are then distributed into the wells of a plate and contacted, in parallel, with the selected antibodies.

The antibodies can bind either cell surface markers or internal proteins. Indeed, it is believed that the binding of exosomes to solid supports such as beads renders certain internal proteins available to outside agents such as antibodies.

Preferably, two or more of the antibodies listed in Table 1 below are used:

TABLE 1

| Antibody | Source Pharmingen |
| --- | --- |
| anti CD11, more preferably | |
| anti CD11c | 30485x |
| anti CD11b | 30455x |
| anti HLA, more preferably anti | |
| HLA abc | 32295x |
| anti CD81 | 33475x |
| anti CD63 | 36585x |
| anti CD58 | 36895x |
| anti CD1a | 34224x |
| anti CD1b | |
| anti CD9 | 30374x |
| anti CD86 | 33409x |
| anti CD82 | 35394x |
| anti CD83 | 36934x |
| anti lactadherin* | — |

*rabbit anti-sera against a lactadherin peptide

Preferably, these antibodies are labeled to allow the detection and/or dosing of the immune complexes formed. Label can be radioactivity, chemical, enzymatic, fluorescent, etc. Preferred labels are fluorescent, such as FITC or PE.

More preferably, at least 5 different antibodies are used, even more preferably at least 8 different antibodies. The antibodies are preferably monoclonal.

In a specific embodiment, the immunophenotyping is performed using direct staining method. A small aliquot of purified exosomes is incubated with anti-Class II (e.g., anti-HLA/DR)-coated magnetic beads. The exosomes coupled to anti-HLA-DR coated magnetic beads are then incubated with labeled antibodies, more preferably fluorescent conjugated (e.g., FITC or PE) monoclonal antibodies. Using flow cytometry, four parameters can be measured. Forward scatter, side scatter, and two fluorescence channels. This two-color flow cytometry analysis permits identification of the antigens on the exosomes in a single measurement.

Results obtained for several dexosome preparations are presented on FIG. 14. These results clearly demonstrate the efficacy and rapidity of the claimed method for immunophenotyping exosome preparations.

Function of Exosomes

A further method was developed to assess the biological activity of membrane vesicles present in a sample (or a purified composition). The method involves assessing the activation of CTL lymphocytes from a population of T cells, using a reference antigen, e.g., the super-antigen (e.g., SEE).

A particular object of this invention thus resides in a method of characterizing the activity of membrane vesicles, comprising contacting super-antigen-loaded vesicles with T cells in the presence of accessory cells, and determining the activation of the T cells.

Superantigens are produced by many different pathogens like bacteria and viruses. Superantigens bind to MHC II molecules directly without being processed. Instead of binding in the groove of the MHC II molecules, superantigens bind to outer surface of MHC II molecules and $V_\beta$ region of T cell receptors (TCR) and are able to stimulate very large numbers of T cells (2–20%). The fact that superantigens can bind to various MHC II and TCR, and induce a strong T cell response make them attractive agents for establishing a general and sensitive assay to test antigen presentation function of dexosomes. Superantigen may be prepared or isolated from various sources. A preferred superantigen for use in the current invention is the SEE antigen, ET 404 (Toxin Technology Inc.). Additional superantigens may be used such as SEA and SEB.

T cells may be any freshly prepared cell population comprising T cells, such as peripheral blood mononuclear cells ("PBMC") for instance, as well as any immortalized T cell line, such as the Jurkat cells. The Jurkat cells are immortalized human T cells, secreting IL-2 upon activation, which can function as the responder cells in this bioassay. The $V_\beta 8$ of TCR of Jurkat cell binds to SEE. As immortal tumor cells, the Jurkat cells are particularly useful since they are much less heterogeneous and easier to grow in the laboratory than primary cells.

Accessory cells may be any cell capable of mediating the activation signal to T cells in the present bioassay. Accessory cells may be dendritic cells, such as any competent primary dendritic cell culture or dendritic cell line. The accessory cells may also be other immune cells or cell lines, in particular antigen presenting cells or cell lines, such as for Raji cells. Raji cells are EBV-immortalized B-cells and have been shown to function in the present bioassay. Raji cells may be cultured in any suitable medium, such as RPMI for instance.

In carrying out the claimed method, superantigen loaded vesicles are contacted with responder T cells in the presence of accessory cells, and T cell activation is assessed.

Measuring the activation of T cells can be performed according to various techniques, such as cytokine release, protein synthesis, responder cell lysis, etc. In a preferred embodiment, T cell activation is measured by determining the cytokine production in the medium, more specifically interleukin-2 production in the medium. Typically, Il-2 is measured by ELISA.

In the method, the membrane vesicles themselves can be loaded with the super-antigen, or the membrane vesicle producing cells (the resulting vesicles then exposing the super-antigen). In a preferred embodiment, the vesicles are contacted with the superantigen.

In a specific embodiment, in this functional assay, super-antigen SEE is first incubated with exosomes prepared from cell culture supernatant by ultrafiltration, cushion density centrifugation, and diafiltration in formulation buffer. Isolated exosomes may be used fresh or can also be stored frozen at −80 degrees in PBS. The complexes of exosome and SEE are then separated from inbound SEE by analytical zonal centrifugation using for instance Optiprep. Optiprep (also known as iodixanol) is a iodinated density gradient media (Nycomed) which allows for a quantitative recovery of exosome/SEE complexes from free SEE. This step is thus important in the biological assay, for quantitative analysis of each prepared exosome lot. The isolated complexes are used to induce T cell activation in the presence of Raji cells as accessory cells. The readout for T cell activation is IL-2 secretion by Jurkat cells.

Particular advantages of the present preparation method over prior art sedimentation techniques using serial centrifugation steps are as follows:

Length of Process Time: Processing by sedimentation is more time consuming in comparison to ultrafiltration and ultracentrifugation. 4 L of tissue culture supernatant would require a minimum of 12 hours to process by sedimentation while a combination of ultrafiltration and a single ultracentrifugation run would take 6–7 hours as it currently run.

Closed System—GMP Compliance: The only centrifugation step in the process is performed on a small volume and can be realized in presently available sealed tubes (capacity of a rotor 6 tubes of 33 ml each). This eliminates the problem, which would have been encountered if a centrifugation step on a large volume (several liter) had to be performed. No sealed centrifugation tubes exist presently for such large volume. Centrifugation should have been done in non disposable open tubes and would not have complied with present regulatory constraints. The clarification, ultrafiltration and sterile filtration are all performed in a biosafety cabinet, and is considered essentially a closed system. Ultracentrifugation is now also performed with sealed tubes, which eliminates the problems that might arise from contamination in an open tube.

Ultrafiltration of Media: Reprocessing of media, such as AIM V, to remove protein aggregates is an important step in the overall process purification scheme. The upstream removal of co-purifying proteins results in a purer exosome product after processing. In particular, it is estimated that the invention allows to produce compositions that are essentially free of aggregates, i.e., wherein aggregates represent less than 2–4% total protein. Furthermore, the removal of haptoglobin reduced undesirable immune responses.

Potential Aggregation of Exosomes After Sedimentation: Sedimentation of exosomes results in a very high local concentration. The high concentration of exosomes in the pellet has the potential to result in an aggregated product. Electron microscopy gives some indication of exosomes being aggregated after sedimentation compared to the method utilizing ultrafiltration. Secondly, it appears that the ultrafiltration of exosomes results in less debris as visualized by electron microscopy.

Process temperature: The process, as of diafiltration, may be performed on ice, i.e., at a temperature of between about 4 to 10° C. This is advantageous since the equilibrium between free peptides and those bound to exosomes through MHCI can be affected by temperature and since such temperatures prevent action of hydrolytic contaminating enzymes such as proteases.

Exosome Purity: Sedimentation of exosomes runs the risk of contamination with cell debris and media contaminants. The removal of contaminant protein aggregates is particularly important because of their high immunogenicity.

Exosome Recovery: The final recovery is 60–75%, significantly greater than the initial sedimentation method (15% average of 9 experiments). This means that the available dose for the treatment of a patient could be increased 5 fold if required or allow to perform apheresis on a smaller volume of blood and cultivate 5 times less cells causing a considerable lowering of the cost of the process.

Additional aspects and advantages of the present invention will be apparent from the following examples, which should be regarded as illustrative and not limitative.

EXAMPLES

1. Preparation of Media

Prior to use, the culture medium (in this example, clinical grade AIM V, a serum-free cell culture medium of Life Technologies, Inc.) has been treated by ultrafiltration to remove aggregated proteins, whose removal does not affect cell growth, but aids considerably in the subsequent isolation of pure dexosomes.

Ultrafiltration of the media was performed using a 500 kDa hollow fiber membrane (from A/G Technology, Needham, Mass. or from a vendor carrying a related product). This membrane size retained the protein aggregates in the retentate while allowing the un-aggregated proteins to pass through with the permeate. The permeate is collected, sterile filtered through 0.22 $\mu$m filter into bottles, and stored at 4° C. until use.

In a specific experiment, to process 50 L of AIM V an UFP-500-C-35A (0.5 mm lumen diameter, 14.5 sq. ft. surface area) hollow fiber cartridge from A/G technology is used. The feed It stream has a flow rate of 13 L/min resulting in a permeate flux of 1 L/min and an inlet and outlet pressure of 12–16 psi and 10 psi, respectively. The process is completed within 1 hour. The permeate is sterile filtered through a 0.22 $\mu$m SartoPore or SartoBran filter (Sartorius Inc). FIGS. 3 and 4 demonstrate the reduced aggregate content of the medium. Quantitation of haptoglobin by ELISA indicates that greater than 99% of haptoglobin related aggregates are removed by ultrafiltration. More particularly, the UF media contains less than about 5 ng/ml of haptoglobin aggregates.

In particular, the BCA assay indicates that ultrafiltration of AIM V media removes 2–4% of the total protein in the media The majority of the fraction of protein removed are aggregates. The protein concentration in the media does not significantly change with the ultrafiltration process, only the concentration of particulates. Pelleting of the ultrafiltered AIM V (UF AIM V) results in any protein pattern substantially different from that observed with un-ultrafiltered AIM V media (see FIG. 3). Furthermore, pelleting of ultrafiltered AIM V 3 months post-processing does not indicate the presence of protein aggregates as indicated by SDS-PAGE (see FIG. 4), confirming that the treated medium can be stored for long periods of time.

Ultrafiltration of albumin (e.g., hSA) compositions also allows to prepare heated hSA products containing less than about 10 ng haptoglobin aggregates per mg of hSA, i.e., less than about 0.001% haptoglobin aggregates (wt).

2. Immature Dendritic Cell Production and Culture

Dendritic cell precursors are harvested from a patient's peripheral blood following leukopheresis. The cell culture procedure is serum free and occurs in clinical grade cell culture media that is further ultrafiltered to remove protein aggregates (or particulate bodies), as described in Example 1. A typical incoming leukopheresis contains about 1 to 2×E10 cells. The cells are washed four times in PBS supplemented with 0.1% human serum albumin (clinical grade) to remove platelets. The cells are then plated into approximately 100–150 cm$^2$ T-flasks at a cell density of 200×10$^6$ cells/flask in serum free ultrafiltered media. The purification of dendritic cell precursors from the leukocytes in the incoming leukopheresis relies on the adhesive properties of monocytes to charged polystyrene surfaces, such as is present in standard commercial tissue culture flasks. After two hours incubation, the monocytes become adherent and are retained while remaining non-adherent cells are discarded with media exchanges using media supplemented with GM-CSF and IL-4 or IL-13 each at 50 ng/mL, as well as gamma interferon. The adherent monocytes undergo differentiation in the presence of GM-CSF and IL-4 or IL-13 to become immature dendritic cells. On Day 5 of culture, these cells are replenished with more GM-CSF and IL-13 or IL-4. Interferon gamma at 500 U/mL may be added to the cells, in order to maintain dendritic cells in an immature status.

3. Procedure for Antigen Loading in a Model System

Preliminary experiments were done to assess the technical parameters for loading antigens into dendritic cells. For this purpose, immature dendritic cells were pulsed with a CMV peptide in order to produce peptide loaded dexosomes. Dexosomes were then isolated by standard procedures and their activity assayed by measuring IFN-$\gamma$ release by a CMV-specific T cell clone. Dexosomes loaded with CMV peptide specifically stimulated the anti-CMV T cell clone and required the presence of dendritic cells, consistent with our findings using the SEE based activity assay (FIG. 2).

Thus using the CMV model system, peptide can be incorporated into dexosomes by the addition of peptide to DC culture on Day 5. Further, our finding that peptide loaded dexosomes require DC for their stimulatory effect on T cells is consistent with the requirement for the inclusion of T cells, DC and dexosomes in the SEE bioassay, thereby underlining the tight correlation between the behavior of dexosomes in these two assays.

4. Clarification

4 L of tissue culture supernatant is harvested and filtered through a 3/0.8 $\mu$m Sartoclean CA (500 cm$^2$ surface area) (Sartorius Inc) at 250 mL/min. The inlet pressure on the filter does not exceed 10 psi (FIG. 5).

5. Concentration

4 L of clarified tissue culture media was concentrated to 100 mL with an UFP-500-C-4A hollow fiber cartridge (0.7 sq. ft. surface area, 0.5 mm lumen diameter) from A/G technology. The feed stream flow rate was between 225–275 mL/min and the inlet and outlet pressure 4–7 psi and 3–6 psi, respectively. The permeate flow rate is between 40–60 mL/min under these conditions. The process required approximately 60–80 min to complete (FIG. 6).

6. Diafiltration

In a specific example, the exosome concentrate was diafiltered against 5 volumes of PBS (i.e. 100 mL dexosome concentrate diafiltered against 500 mL of PBS). A SDS-PAGE of concentrated dexosomes before and after diafiltration is depicted in FIG. 7. This step, as well as all subsequent steps were performed at chilled conditions (between about 4–10° C.).

7. Density Cushion Separation (Discontinuous Gradient)

In a specific example, the concentrated and diafiltered culture medium containing exosomes, as well as those examples where the exosome have been pulsed with antigen(s), is purified by (ultra)centrifugation on a density cushion as follows: The exosome concentrate (approximately 100 mL) is equally aliquoted into centrifuge tubes and underlayed with 4 mL of a sucrose/Tris D2O buffer. The $D_2O$ density cushion consists of 25–30% sucrose/20 mM Tris $D_2O$ (w/w %)(pH 7.5–7.7). The density is between 1.18 and 1.21 g/ml. The tubes are sealed to ensure a closed system.

FIG. 9a depicts a SDS-PAGE of the sample before and after ultracentrifugation as well as the content above the cushion, in the cushion, or in the pellet. As shown, the majority of the protein does not sediment into the sucrose/Tris $D_2O$ density cushion. This is further confirmed on FIG. 9b, which demonstrates that at least 90% of the exosomes are recovered in the cushion.

8. Formulation and Conditioning

The purified exosomes were subjected to buffer exchange by diafiltration with a 500 kDa ultrafiltration hollow fiber cartridge identical in format to that used previously for concentration and/or diafiltration (see examples 5 and 6). The cartridge was pre-conditioned with hSA (e.g. 100 ug/mL) for a minimum of 15 min prior to diafiltration and sized for the processing of 10–20 mL of media. A typical SDS-PAGE of a dexosome sample at $1/2800^{th}$ its original volume is depicted in FIG. 10.

The formulated exosomes were sterile filtrated through 0.22 μm syringe filter (Millex GV (25 mm syringe)).

The amount of haptoglobin aggregates present in the exosome preparation (200-fold concentration from original media) conditioned in a PBS buffer was measured by ELISA and determined to be essentially below about 0.1 ng/ml, more specifically 0.091 ng/ml or 0.044 ng/ml for the two preparations tested. In comparison, the content of aggregated haptoglobin in exosome preparation obtained according to prior published methods, after an identical 200-fold concentration, was found by ELISA to be 400 μg/ml. This corresponds to a quantitative recovery of the haptoglobin aggregates present in the unpurified AIMV medium (2 μg/ml). Thus, the method of this invention, as compared to the prior art methods, leads to a 5 to 10 millions fold decrease of haptoglobin aggregates contamination in exosome preparations (400 μg/ml versus 40–90 pg/ml). Since ultrafiltration of the media reduces the content of haptoglobin aggregates by a factor of about five hundreds, the additional ultrafiltration, diafiltration and/or density cushion steps also contribute very significantly to the increased purification performance. These results further illustrate the efficacy of the present methods in removing haptoglobin aggregates.

Dosing of Exosomes

In a specific embodiment, ELISA-based analyses have been developed in order to provide a quantitative measure of exosomes in a sample, composition, fluid, etc. FIG. 11 illustrates the measurement of HLA-DR (i.e. MHC II) (11b) and CD81 (11a) in dexosomes. The HLA/DR assay is both sensitive and functionally relevant to the activity of dexosomes. This assay was chosen as the quantitation assay for dexosomes preparation. The assay is described in detail below.

The HLA/DR signal measured by ELISA is used to determine the number of MHC II molecules obtained from a dexosome preparation. The number of MHC II associated with a number of cell types has been reported previously (Cella et al 1997). These values are summarized in Table 2.

TABLE 2

Approximate numbers of MHC II molecules per cell number (adapted from Cella et al 1997)

| Cell Type | MHC II molecules/cell (× E6) |
|---|---|
| Fresh monocytes | <0.1 |
| Cultured monocytes | <1.0 |
| Raji cells | 2.0 |
| Immature DC | 5.2 |
| Mature DC | 8.3 |

To quantitate the amount of HLA/DR molecules, DC lysate or Raji cell lysate is used as standards. FIG. 11 shows a titration of anti-HLA/DR at a fix concentration of immature DC lysate. From this plot, the number of HLA/DR molecules to immature dendritic cells is calculated to be $5.8 \times 10^6$ molecules/cell, which is in agreement with the literature value presented in Table 1. An identical result was obtained for Raji cell lysate (data not shown).

An example of the HLA/DR assay results obtained from a dexosome preparation is depicted in FIG. 12(A,B). The HLA/DR signal is plotted as a function of the equivalent supernatant volume. The number of HLA/DR molecules/uL dexosome was determined to be $4.7 \times 10^{10}$ after ultracentrifugation onto a density cushion (i.e. UC-cushion) and diafiltration into formulation buffer. The % recovery for that sample was 73% HLA/DR. More particularly, the % recovery was as follows:

| Process Step | Overall % Recovery |
|---|---|
| Clarification through 0.8 μm | 100% |
| $1^{st}$ Ultrafiltration - Concentration | 100% |
| $1^{st}$ Ultrafiltration - Diafiltration | 86 +/− 2% |
| Cushion - $2^{nd}$ Ultrafiltration - Diafiltration | 85 +/− 2% |
| 0.2 μm Sterile Filtration | 75 +/− 3% |

In summary, the ELISA assay for HLA/DR determination quantifies dexosomes in the final product. Since this assay can also measure HLA/DR on dendritic cells, this assay provides a means for relating HLA/DR dose per dendritic cell and per volume of isolated dexosome. In this regard, we are generally able to generate a minimum of 100,000 HLA/DR molecules per immature DC after purification (10–12 experiments).

A similar assay was performed using an anti-class I antibody for capture, namely the antibody produced by HC-10 cells. The results are presented on FIGS. 12(C,D). From the titration curve (12C), the amount of MHC-I molecules can be determined from any unknown exosome preparation (12D).

10. Phenotyping of Exosomes 5 to 10 μl of anti-HLA-DR-coated magnetic beads are washed in a microfuge tube with 500 μl of PBS using a magnetic rack. The supernatant is discarded and 25, 50 or 100 μl of concentrated exosome preparation are added to the washed beads (exosome concentration may be up to 1000 times). The mixture is incubated at 4° C. for about 2 hours on a rotating plate. After incubation, 500 μl PBS are added to the exosome-coupled beads and the beads are washed using the magnetic rack. The supernatant is removed and the exosome-coupled beads are suspended in 200 μl of staining buffer. 20 μl of the exosome-coupled beads solution are aliquoted in test tubes which are then contacted each separately with one of the labeled antibodies selected for analysis. The antibodies are incubated for about 30 minutes at 4° C. The tubes are then added with staining buffer and centrifuged at 1200 rpm for 5 minutes. The supernatant is discarded and a fixative solution is added (0.5 ml) in each tube. Each assay tube is then acquired and analyzed by flow cytometry using a FACSCalibur™ apparatus.

Results obtained for several dexosome preparations are presented on FIG. 13. These results clearly demonstrate the efficacy and rapidity of the claimed method for immunophenotyping exosome preparations.

11. Functional Assay

Approximately 20 µl of isolated dexosomes are needed for each test. Dexosomes are incubated with SEE at 100 ng/ml (10 µl of a stock of 1 µg/ml SEE in PBS with 0.1% BSA) in the final volume of 100 µl for 1 hour at 37 degrees. After the 1 hour incubation, complexes of dexosome and SEE (dexosome/SEE) are separated from unbound SEE by zonal ultracentrifugation (2.2 mL) onto a two step discontinuous gradient composed of Optiprep solutions (FIGS. 14–16).

The Optiprep gradient is made by first adding 1.7 ml of 10% Optiprep (1.67 ml Optiprep plus 8.33 ml RPMI) into each test tube. Next, 100 µl of 20% Optiprep (3.33 ml Optiprep plus 6.67 ml RPMI) are added to the bottom of each tube, followed by addition of 100 µl of 40% Optiprep (6.67 ml Optiprep plus 3.33 ml RPMI) below the 20% Optiprep. Exosome/SEE samples are then layered onto the top of the gradient in a final volume of 200 µl in 0.1% BSA in PBS. The tubes are centrifuged for 40 minutes at 100,000 rpm at 4 degrees using slow acceleration and deceleration in a swinging bucket rotor (TLS-55). 200 µl of samples are collected from the bottom of the tube, which contains the complexes of exosome/SEE freed of unbound SEE. Free SEE remains in the zonal layer (10% Optiprep), while the exosomes/SEE complex sediments into the 20–40% region of the tube.

Raji cells, dexosome/SEE (or mock/SEE), and then Jurkat cells are added into wells of a plate (100 µl (30,000 cells) of each kind of cells is used for each well). Positive and negative 5 controls are also added: Jurkat cells alone (negative control), Jurkat plus 1 ng/well SEE (negative control), Raji alone (negative control), Raji and Jurkat plus dexosomes un-pulsed with SEE (background control), Raji and Jurkat plus 1 ng/well SEE (positive control). The plate is incubated for 18 hours 37 degrees with 5% CO2. The cell culture supernatant is collected from each of the wells of the plate by centrifugation at 1200 rpm (use plate carriers) for 15 minutes. 200 µl of the supernatant are used in an ELISA assay to measure IL-2 secretion. The ELISA assay may be performed immediately or later (in which case the plate can be wrapped in parafilm and frozen until use).

The IL2 ELISA assay is performed using the IL-2 ELISA kit (Duo set DY202, R&D Systems) in Costar ELISA plates (Costar 2581), following instructions of the manufacturer. The results show a dose-dependent relationship between IL2 secretion and the amount of exosomes per well, which has been converted to the volume equivalent to that of exosome stock. IL2 secretion is SEE-dependent, because exosomes require SEE to stimulate non antigen-specific T cells (e.g., Jurkat). The unit of half-max is introduced as a semi-quantitative measurement for dexosome's titre in the method. It is defined as the volume of exosome at which the half maximum IL2 secretion by Jurkat cells is reached under the used experimental conditions. A smaller half-max unit measured is indicative of a higher titre.

What is claimed is:

1. A method of preparing membrane vesicles, comprising:
   a. culturing a population of antigen-presenting cells under conditions allowing a release of membrane vesicles by antigen-presenting cells;
   b. enriching the membrane vesicles; and
   c. isolating the membrane vesicles using density cushion centrifugation.

2. The method of claim 1, wherein the antigen presenting cells are immature dendritic cells.

3. The method of claim, 1, further comprising a diafiltration of the preparation from step c.

4. The method of claim 1, wherein the enrichment step comprises a clarification.

5. The method of claim 1, wherein the enrichment step comprises a concentration by ultrafiltration.

6. The method of claim 1, wherein the enrichment step comprises a clarification and a concentration by ultrafiltration.

7. The method of claim 1, wherein the enrichment step comprises a diafiltration by ultrafiltration.

8. The method of claim 1, further comprising a sterile filtration of the preparation from step c.

9. A method for preparing membrane vesicles, comprising:
   a. obtaining a population of antigen-presenting cells;
   b. sensitizing the antigen-presenting cells to one or several antigens;
   c. culturing the population of antigen-presenting cells under conditions allowing the release of membrane vesicles by antigen-presenting cells;
   d. a clarification of the culture supernatant;
   e. a concentration of the clarified supernatant;
   f. a diafiltration of the concentrated supernatant;
   g. the isolation of the membrane vesicles using density cushion centrifugation in a cushion buffer;
   h. diafiltration to exchange the cushion buffer with a formulation buffer; and
   i. a sterile filtration of the vesicle membranes obtained in h.

* * * * *